(12) United States Patent
Dhesy-Thind et al.

(10) Patent No.: US 10,576,056 B2
(45) Date of Patent: Mar. 3, 2020

(54) COMPOUNDS FOR TREATING CANCER AND METHODS OF USE THEREOF

(71) Applicant: MCMASTER UNIVERSITY, Hamilton (CA)

(72) Inventors: Sukhbinder Dhesy-Thind, Burlington (CA); Katarzyna J. Jerzak, Toronto (CA); Anita Bane, Hamilton (CA); Jessica G. Cockburn, Calgary (CA); John A. Hassell, Dundas (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 16/063,622

(22) PCT Filed: Dec. 22, 2016

(86) PCT No.: PCT/CA2016/051530
§ 371 (c)(1),
(2) Date: Jun. 18, 2018

(87) PCT Pub. No.: WO2017/106974
PCT Pub. Date: Jun. 29, 2017

(65) Prior Publication Data
US 2018/0369190 A1    Dec. 27, 2018

Related U.S. Application Data

(60) Provisional application No. 62/387,200, filed on Dec. 24, 2015.

(51) Int. Cl.
*A61K 31/343*    (2006.01)
*A61K 31/12*    (2006.01)
(Continued)

(52) U.S. Cl.
CPC ............ *A61K 31/343* (2013.01); *A61K 31/12* (2013.01); *A61K 31/192* (2013.01); *A61K 45/06* (2013.01);
(Continued)

(58) Field of Classification Search
None
See application file for complete search history.

(56) References Cited

U.S. PATENT DOCUMENTS 5,883,294 A    3/1999    Scanlan et al.

FOREIGN PATENT DOCUMENTS

WO    2004089470 A2    10/2004
WO    2012032545 A1    3/2012

OTHER PUBLICATIONS

Cortes et al. Eribulin monotherapy versus treatment of physician's choice in patients with metastatic breast cancer (EMBRACE): a phase 3 open-label randomised study. Lancet, 2011; 377: 914-923.*

(Continued)

*Primary Examiner* — Anna Pagonakis
(74) *Attorney, Agent, or Firm* — Bereskin & Parr LLP/S.E.N.C.R.L., S.R.L.; Sandra Marone

(57) ABSTRACT

Two isoforms of thyroid receptor alpha (THRα1 and THRα2) have been found to be associated with the growth of cancer. Use of inhibitors of THRα1 (Formula I) and/or agonists of THRα2 (Formula II) in the treatment of such cancers is disclosed. Treatment of other disorders associated with such receptors is also contemplated, as is the use of diagnostic methods for predicting therapeutic outcomes based on the levels of expression of THRα1 and THRaα2 in a tissue sample.

(Continued)

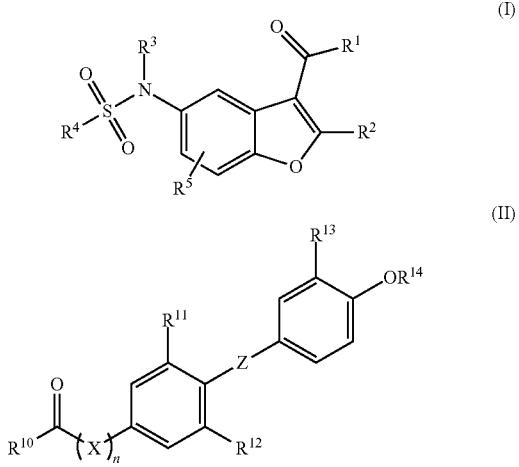

3 Claims, 17 Drawing Sheets

(51) Int. Cl.
- A61K 31/192 (2006.01)
- A61K 45/06 (2006.01)
- C07C 49/215 (2006.01)
- C07D 307/80 (2006.01)
- C07C 59/68 (2006.01)
- A61P 35/00 (2006.01)
- A61P 5/14 (2006.01)

(52) U.S. Cl.
CPC ............... *A61P 5/14* (2018.01); *A61P 35/00* (2018.01); *C07C 49/215* (2013.01); *C07C 59/68* (2013.01); *C07D 307/80* (2013.01)

(56) References Cited

OTHER PUBLICATIONS

International Search Report and Written Opinion of corresponding PCT Application No. PCT/CA2016/051530 dated Apr. 26, 2017.
Jerzak et al., "Thyroid Hormone Receptor α in Breast Cancer: Prognostic and Therapeutic Implications". Breast Cancer Research and Treatment (2015), vol. 149, Issue 1, Dec. 27, 2014, pp. 293-301.
Nina Ditsch et al., "Thyroid Hormone Receptor (TR) alpha and TRbeta Expression in Breast Cancer", Histology Histopathology, 2013, vol. 28, pp. 227-237.
H.C. Van Beeren, "Dronerarone Acts as a Selective Inhibitor of 3,5,3'—Triiodothyronine Binding to Thyroid Hormone Receptor-α1: In Vitro and in Vivo Evidence", Endocrinology, vol. 144, pp. 552-558, Feb. 2003.
Han et al., "Preparation of Solid Dispersion of Dronedarone Hydrochloride with Soluplus® by Hot Melt Extrusion Technique for Enchanced Drug Release", Chem. Pharm. Bull, 63, 295-299, 2015.
Dinda, et al., "Estrogen-like effects of thyroid hormone on the regulation of tumor suppressor proteins, p53 and retinoblastoma, in breast cancer cells", Oncogene (2002), 21, 761-768.
Nogueira, et al., "Triiodothyronine Mimics the Effects of Estrogen in Breast Cancer Cell Lines", J. Steroid Biochem., Molec. Biol., vol. 59, No. 3/4, pp. 271-279, 1996.
Hercbergs, Aleck, "Spontaneous remission of cancer—a thyroid hormone dependent phenomenon, HercbergsA1", Anticancer Res. Nov.-Dec. 1999; 19(6A): 4839-44.
Hercbergs, et al., "Medically Induced Euthyroid Hypothyroxinemia May Extend Survival in Compassionate Need Cancer Patients: An Observational Study", The Oncologist, 2015; 20:72-76.
Angelousi, et al., "Primary HT and risk for breast cancer: a systematic review and meta-analysis", European Journal of Endocrinology, 2012, 166, 373-381.
Furuya, et la., "Liganded Thyroid Hormone Receptor-a Enhances Proliferation of Pancreatic β-Cells", J. Biol. Chem. 285:24477-24486.
Hellevik, et al., "Thyroid Function and Cancer Risk: A Prospective Population Study", Cancer Epidemiol Biomarkers Prev. 18:570-574.
Tosovic, et al., "Prospectively measured triiodothyronine levels are positively associated with breast cancer risk in postmenopausal women", Breast Cancer Research, 2010, 12: R33.
De Sibio, et al, "Triiodothyronine and breast cancer",World J. Clin. Oncol., Aug. 10, 2014; 5(3): 503-508.
Gu, et al, "Targeting Thyroid Receptor β in Estrogen Receptor Negative Breast Cancer" (Abstract), Cancer Res., 2012, 72(24 Suppl): 49s.
European Search Report and Written Opinion of corresponding European Patent Application No. 16877052.7 dated Jul. 17, 2019.
Zhi-Hong Yu et al., "Small Molecule Inhibitors of SHP2 Tyrosine Phosphatase Discovered by Virtual Screening", Bloorganic & Medicinal Chemistry Letters, May 20, 2011, vol. 21, No. 14, pp. 4238-4242.
Andrea Perra et al., "Thyroid Hormone Receptor Ligands Induce Regression of Rat Preneoplastic Liver Lesions Causing Their Reversion to a Differentiated Phenotype", Hepatology, Nov. 19, 2008, vol. 49, No. 4, pp. 1287-1296.
Anil Belur Nagaraj et al., "Evaluating Class III Antiarrhythmic Agents as Novel MYC Targeting Drugs in Ovarian Cancer", Gynecologic Oncology, Oct. 6, 2018, vol. 151, No. 3, pp. 525-532.
Mitchell J. Elliott et al., "The Antiarrhythmic Drug, Dronedraone, Demonstrates Cytotoxic Effects in Breast Cancer Independent of Thyroid Hormone Receptor Alpha 1 (THR[alpha])1) Antagonism", Scientific Reports, Nov. 8, 2018, vol. 8, No. 1, pp. 1-10.
Grazia Chiellini et al., "A High-Affinity Subtype-Selective Agonist for the Thyroid Hormone Receptor", Chemistry and Biology, Jan. 1, 1998, vol. 5, No. 6, pp. 299-306.

* cited by examiner

Cohort #1 (130 unselected breast cancer patients)

Cohort #2 (158 patients with triple negative breast cancer)

a, p< 0.05
b, p=0.051
c, p < 0.1

For T4: all arrows denote p< 0.05

P-value:

| | |
|---|---|
| Doc/Vehicle | 0.000264583 |
| T3/vehicle | 0.904795804 |
| Dr/vehicle | 0.002429708 |
| Doc+Dr/Vehicle | 3.91796E-05 |
| Doc+T3/Dr+T3 | 0.007039681 |
| Doc+T3/T3 | 0.049225872 |
| Doc+Dr/Dr | 0.000159094 |
| Doc+Dr/Doc | 0.00331394 |

*Doc = docetaxel, Dr = dronedarone, T3 = tri-iodothyronine.

P-value:

| | |
|---|---|
| Tmx+T3/Tmx alone | 2.8035E-05 |
| Tmx+Dr+T3/Tmx+Dr | 1.56812E-06 |
| Tmx+Dr+T3/Vehicle | 9.79157E-05 |
| Tmx/Vehicle | 0.000245939 |
| Dr+T3/Vehicle | 0.000206839 |
| Dr/Vehicle | 0.000588201 |

*Tmx = tamoxifen, Dr = dronedarone, T3 = tri-iodothyronine.

(a)

(b)

(c)

COMPOUNDS FOR TREATING CANCER AND METHODS OF USE THEREOF

CROSS-REFERENCE TO RELATED APPLICATIONS

This application is a National Stage of co-pending International Application No. PCT/CA2016/051530 filed on Dec. 22, 2016 which claims the benefit of priority from U.S. Provisional Patent Application No. 62/387,200 filed on Dec. 24, 2015, the contents of both of which are incorporated herein by reference in their entirety.

FIELD

The present application relates to compounds targeting the thyroid receptor alpha (THRα) isoforms for the prognosis and treatment of, for example, various cancers. The application further relates to pharmaceutical compositions and uses comprising the compounds of the application.

BACKGROUND

Thyroid hormones (TH), triiodothyronine (T3) and thyroxine (T4), play crucial roles in regulating cellular processes such as proliferation and metabolism, through binding to their cognate thyroid hormone receptors THRα and THRβ. THR's form homodimers or heterodimers with retinoid X receptors; when bound by TH, they act as classical transcription factors by binding to the promoter regions of target gene (FIG. 1).

Thyroid hormones are endogenous modulators of malignant tumors, including breast tumors. Indeed, increased thyroid hormone expression was positively correlated with overall breast cancer risk. While THRα is expressed in diverse normal and malignant tissues, little is known about its clinical relevance and specifically the relevance of alternatively spliced THRα isoforms, THRα1 and THRα2, in breast cancer. THRα1 binds to the thyroid hormone and mediates its biological effects, but THRα2 lacks the binding site for thyroid hormone and consequently functions as a weak antagonist of thyroid hormone signaling (FIG. 2).

Women whose tumors had high expression of THRα2 lived longer and had fewer breast cancer recurrences than those with low expression, particularly when THRα1 expression was concomitantly low [1]. This suggests that THRα2 may be protective and that THRα1 may be detrimental for breast cancer recurrence and survival. Biological rationale supports a differential effect of THRα1 and THRα2 expression on clinical outcomes. When THRα1 binds TH, it mediates transcription and expression of target genes [2, 3]. THRα2, on the other hand, is unable to bind TH because it lacks a ligand-binding domain [4-8]. Hence, it acts a constitutive transcriptional repressor and it may reduce the expression of p53, retinoblastoma and other growth-promoting genes in breast cancer [9].

Similar to reduction of estradiol levels in estrogen receptor (ER) positive breast cancers, it is conceivable that lowering TH levels may be therapeutic in THR-expressing cancers. Given their indispensable and life-sustaining roles, however, patients are unlikely to tolerate marked reductions in TH levels [6].

SUMMARY

The present application includes prognostic and therapeutic methods in targeting THRα isoforms, for example, for the treatment of various cancers.

One aspect of the present application includes a method of treating a disease, disorder or condition that benefits from inhibition of THRα1, comprising administering an effective amount of one or more compounds of Formula (I), or a pharmaceutically acceptable salt and/or solvate thereof, to a subject in need thereof, wherein the compounds of the Formula (I) are:

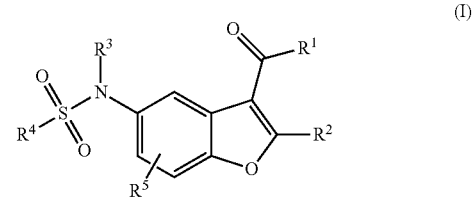

wherein
$R^1$ is selected from $C_{1-6}$alkyl, halo$C_{1-6}$alkyl, $OC_{1-6}$alkylene, $OC_{1-6}$alkylene-$OC_{1-6}$alkyl, $OC_{1-6}$alkylenearyl, OH and unsubstituted or substituted aryl; the substituents on $R^1$ are selected from $OC_{1-6}$alkylene-$NR^6R^7$ and $OC_{1-6}$alkylene-$N(O)R^6R^7$;
$R^2$ is selected from $C_{1-6}$alkyl, aryl and $C_{1-6}$alkylene-$OC_{1-6}$ alkyl;
$R^3$ is selected from H, $C_{1-6}$alkyl and $SO_2R^8$;
$R^4$ is selected from $C_{1-6}$alkyl, halo$C_{1-6}$alkyl and unsubstituted or substituted aryl;
the substituents on $R^4$ are selected from one or more of halo, $C_{1-6}$alkyl, $OC_{1-6}$alkylene, $NR^9C(O)C_{1-6}$alkyl and COOH;
$R^5$ is selected from H, halo and $C_{1-6}$alkyl;
$R^6$, $R^7$, $R^8$ and $R^9$ are independently selected from one or more of H and $C_{1-6}$alkyl; and
one or more available hydrogens are optionally replaced with D and/or F;
or a salt and/or solvate thereof.

Another aspect of the present application includes a method of treating a disease, disorder or condition that benefits from inhibition of THRα1, comprising administering an effective amount of one or more compounds of Formula (Ia), or a pharmaceutically acceptable salt and/or solvate thereof, to a subject in need thereof, wherein the compounds of the Formula (Ia) are:

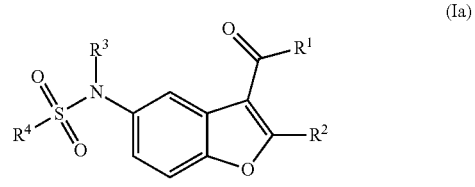

wherein
$R^1$ is selected from $C_{1-6}$alkyl, halo$C_{1-6}$alkyl, $OC_{1-6}$alkylene, $OC_{1-6}$alkylene-$OC_{1-6}$alkyl, $OC_{1-6}$alkylenearyl, OH and unsubstituted or substituted aryl;
the substituents on $R^1$ are selected from $OC_{1-6}$alkylene-$NR^6R^7$ and $OC_{1-6}$alkylene-$N(O)R^6R^7$;
$R^2$ is selected from $C_{1-6}$alkyl, aryl and $C_{1-6}$alkylene-$OC_{1-6}$alkyl;
$R^3$ is selected from H, $C_{1-6}$alkyl and $SO_2R^8$;
$R^4$ is selected from $C_{1-6}$alkyl, halo$C_{1-6}$alkyl and unsubstituted or substituted aryl;

the substituents on $R^4$ are selected from one or more of halo, $C_{1-6}$alkyl, $OC_{1-6}$alkylene, $NR^9C(O)C_{1-6}$alkyl and COOH;

$R^6$, $R^7$, $R^8$ and $R^9$ are independently selected from one or more of H and $C_{1-6}$alkyl; and one or more available hydrogens are optionally replaced with D and/or F;

or a salt and/or solvate thereof.

In a further aspect of the application there is provided a method of inhibiting THRα1 comprising administering an effective amount of one or more compounds of Formula (I) or one or more compounds of Formula (Ia) as defined above, or a pharmaceutically acceptable salt and/or solvate thereof, to a subject in need thereof.

In another aspect of the application there is included a pharmaceutical composition for treating a disease, disorder or condition that benefits from inhibition of THRα1 comprising one or more compounds of Formula (I) or one or more compounds of Formula (Ia) as defined above, or a pharmaceutically acceptable salt and/or solvate thereof, and a pharmaceutically acceptable carrier and/or diluent.

In another aspect of the application there is included a method of treating a disease, disorder or condition that benefits from inhibition of THRα1 comprising administering, to a subject in need thereof, one or more compounds of Formula (I) or one or more compounds of Formula (Ia) as defined above, or a pharmaceutically acceptable salt and/or solvate thereof, in combination with one or more other therapies for treating the disease, disorder or condition that benefits from inhibition of THRα1.

A further aspect of the present application includes a method of treating a disease, disorder or condition that benefits from the upregulation of THRα2, comprising administering an effective amount of one or more compounds of Formula (II), or a pharmaceutically acceptable salt and/or solvate thereof, to a subject in need thereof, wherein the compounds of Formula (II) are:

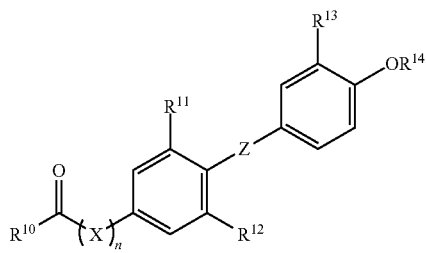

wherein $R^{10}$ is selected from OH, $C_{1-6}$alkyl, $OC_{1-6}$alkyl and halo$C_{1-6}$alkyl;

$R^{11}$, $R^{12}$ and $R^{13}$ are independently selected from H, halo, $C_{1-6}$alkyl and $OC_{1-6}$alkyl;

$R^{14}$ is selected from H, halo and $C_{1-6}$alkyl;

X is selected from NH, O, $C_{1-6}$alkylene, $OC_{1-6}$alkylene and $C_{1-6}$alkylene-O;

n is 1 or 2;

Z is selected from NH, O and $C_{1-6}$alkylene; and one or more available hydrogens are optionally replaced with D and/or F;

or a salt and/or solvate thereof;

with proviso that when X is O, n is not 2.

In a further aspect of the application there is included a method of upregulating THRα2 comprising administering an effective amount of one or more compounds of Formula (II) as defined above, or a pharmaceutically acceptable salt, and/or solvate thereof, to a subject in need thereof.

In another aspect of the application there is provided a pharmaceutical composition for treating a disease, disorder or condition that benefits from the upregulation of THRα2 comprising one or more compounds of Formula (II) as defined above, or a pharmaceutically acceptable salt and/or solvate thereof, and a pharmaceutically acceptable carrier and/or diluent.

In another aspect of the application there is included a method of treating a disease, disorder or condition that benefits from the upregulation of THRα2 comprising administering, to a subject in need thereof, one or more compounds of Formula (II) as defined above, or a pharmaceutically acceptable salt and/or solvate thereof, in combination with one or more other therapies for treating the disease, disorder or condition that benefits from the upregulation of THRα2.

A further aspect of the present application includes a method of treating a subject having a THRα-expressing cancer comprising administering an effective amount of a THRα1 inhibitor and an effective amount of a THRα2 upregulator, to the subject.

A further aspect of the present application includes a method of treating a subject having a THRα-expressing cancer comprising administering an effective amount of a compound of Formula (I) as defined above, or a salt and/or solvate thereof, and an effective amount of a compound of Formula (II) as defined above, or a salt and/or solvate thereof, to the subject.

In some embodiments, rather than reducing TH levels in patients having THR-expressing cancers, the present application is directed to modulating the expression of nuclear THRs in cancer cells as a viable option for personalized cancer care.

The present application also includes a method for predicting the therapeutic outcome of subjects having a THRα-expressing cancer comprising measuring the expression of THRα2 and THRα1 transcript variants in biological samples from the subjects, wherein an increase in THRα2 transcript variants and/or a decrease in THRα1 transcript variants compared to controls is predictive of a positive therapeutic outcome and a decrease in THRα2 transcript variants and/or an increase in THRα1 transcript variants compared to controls is predictive of a negative therapeutic outcome. In an embodiment the method further comprises treating subjects with a decrease in THRα2 transcript variants and/or an increase in THRα1 transcript variants compared to controls, identified using the method, with an effective amount of one or more compounds of the application.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which.

DETAILED DESCRIPTION

I. Definitions

Figure 1:
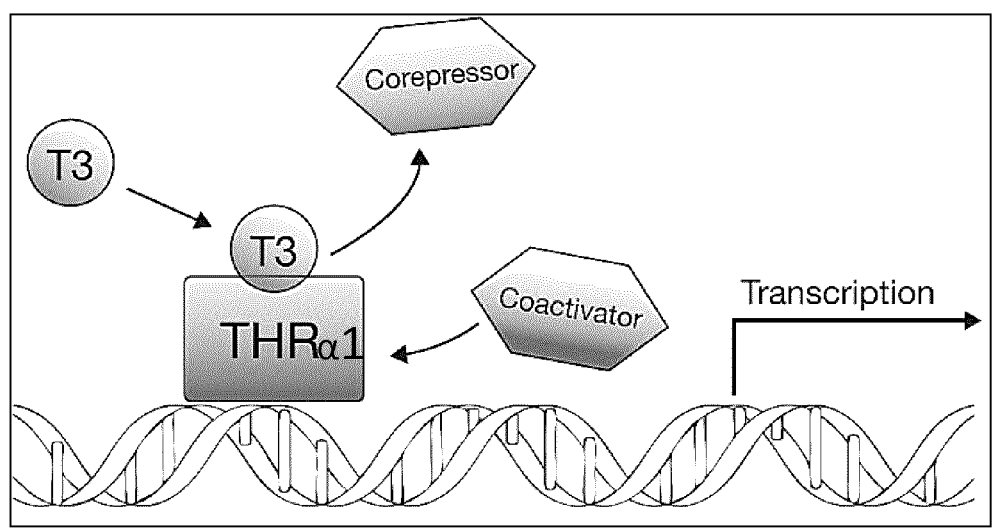
FIG. 1 shows a conceptual model whereby the thyroid hormone receptor (THRα1) acts as transcription factor, with thyroid hormone (predominantly 3-iodothyronine) influencing the rate of transcription via recruitment of co-activators as opposed to co-repressors. Thyroid hormone receptors influence the expression of a variety of different growth-promoting genes, as well as tumour suppressors—p53 and retinoblastoma.
Figure 2:
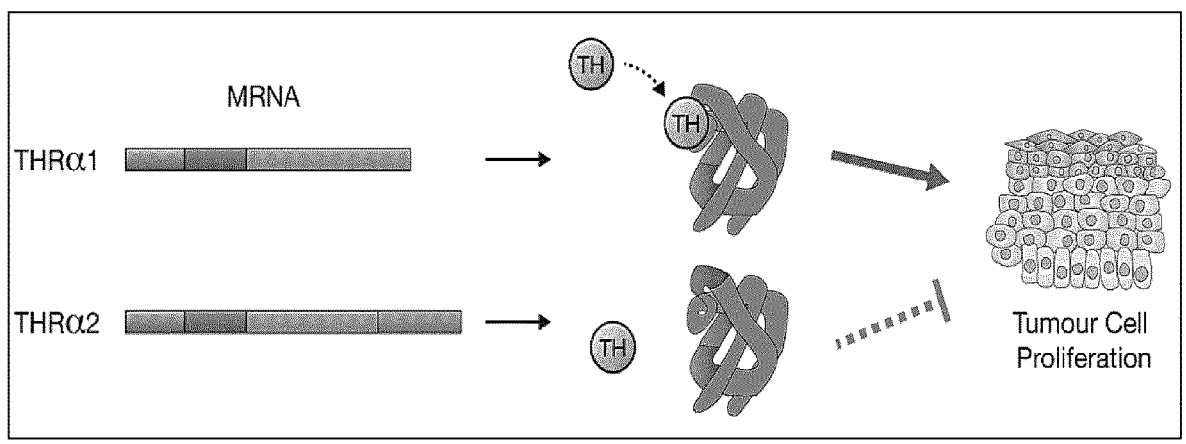
FIG. 2 is a conceptual model illustrating that THRα2 is unable to bind thyroid hormone (TH), opposing THRα1-driven transcription and its proposed effect on tumor cell proliferation.

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical terms and abbreviations used by those skilled in the art. Nevertheless, definitions of selected terms are provided for clarity and consistency.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms. It is an embodiment of the application that, in the alkyl groups, one or more, including all, of the available hydrogen atoms are optionally replaced with F or $^2$H and thus include, for example trifluoromethyl, pentafluoroethyl and the like.

The term "alkylene" as used herein, whether it is used alone or as part of another group, means straight or branched chain, saturated alkylene group; that is a saturated carbon chain that contains substituents on two of its ends. The number of carbon atoms that are possible in the referenced alkylene group are indicated by the numerical prefix "$C_{n1-n2}$". For example, the term $C_{1-6}$alkylene means an alkylene group having 1, 2, 3, 4, 5, or 6 carbon atoms. It is an embodiment of the application that, in the alkylene groups, one or more, including all, of the available hydrogen atoms are optionally replaced with F or $^2$H.

The term "haloalkyl" as used herein refers to alkyl groups as defined above in which one or more of the available hydrogen atoms are replaced with a halogen.

The term "aryl" as used herein, whether it is used alone or as part of another group, refers to mono-, bi- or tricyclic groups that contain at least one aromatic carbocycle. In an embodiment of the present application, the aryl group contains 6, 9, 10 or 14 carbon atoms, such as phenyl, naphthyl, indanyl or anthracenyl. It is an embodiment of the application that, in the aryl groups, one or more, including all, of the available hydrogen atoms are optionally replaced with F or $^2$H and thus include, for example pentafluorophenyl and the like.

The term "halo" as used herein refers to a halogen atom and includes F, Cl, Br and I.

The term "available hydrogen atoms" refers to atoms that would be known to a person skilled in the art to be capable of replacement by either a fluorine, other halogen or deuterium using methods known in the art.

The term "solvate" as used herein means a compound of the Formula (I) or Formula (II) or a pharmaceutically acceptable salt of a compound of the Formula (I) or Formula (II), wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

The term "compound(s) of the application" or "compound(s) of the present application" as used herein includes a compound of the Formula (I), I(a) and (II) and salts and/or solvates thereof.

The term a "therapeutically effective amount", "effective amount" or a "sufficient amount" of a compound of the present invention is a quantity sufficient to, when administered to the subject, including a mammal, for example a human, effect beneficial or desired results, including clinical results, and, as such, an "effective amount" or synonym thereto depends upon the context in which it is being applied. In the context of disease, therapeutically effective amounts of the compounds of the present invention are used to treat, modulate, attenuate, reverse, or affect a disease or conditions for example, cancer in a subject. An "effective amount" is intended to mean that amount of a compound that is sufficient to treat, prevent or inhibit such diseases or conditions. The amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses or reduces a disease or conditions for example, cancer as determined by clinical symptoms or the amount of cancer cells, in a subject as compared to a control. As defined herein, a therapeutically effective amount of a compound of the present invention may be readily determined by one of ordinary skill by routine methods known in the art.

The term "pharmaceutically acceptable" means compatible with the treatment of animals, in particular, humans.

The term "pharmaceutically acceptable salt" means an acid addition salt or base addition salt, which is suitable for or compatible with the treatment of patients.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Moreover, a "treatment" or "prevention" regime of a subject with a therapeutically effective amount of the compound of the present invention may consist of a single administration, or alternatively comprise a series of applications. For example, the compound of the present invention is administered at least once a week. However, in another embodiment, the compound is administered to the subject from about one time per week to about once daily for a given treatment. In yet another embodiment the compound is administered more than once daily up to 5 times per day. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration is required.

To "inhibit" or "suppress" or "reduce" a function or activity, is to reduce the function or activity when compared to otherwise same conditions except for a condition or parameter of interest, or alternatively, as compared to another condition. The terms "inhibitor" and "inhibition", in the context of the present application, are intended to have a broad meaning and encompass compounds of the application which directly or indirectly (e.g., via reactive intermediates, metabolites and the like) act on diseases, disorders or conditions that benefit from THRα regulation, such as THRα-expressing cancers.

To "upregulate" or "induce" or "increase" a function or activity, is to increase the function or activity when compared to otherwise same conditions except for a condition or parameter of interest, or alternatively, as compared to another condition. The terms "upregulator" and "upregulation", in the context of the present application, are intended to have a broad meaning and encompass compounds of the application which directly or indirectly (e.g., via reactive intermediates, metabolites and the like) act on diseases, disorders or conditions that benefit from THRα regulation, such as THRα-expressing cancers.

The term "subject" as used herein includes all members of the animal kingdom including human. The subject is preferably a human.

The term "cancer" as used herein refers to a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. Reference to cancer includes reference to cancer cells.

The term "patient outcome" refers to a condition of a patient following a treatment, therapeutic or disease course.

The term "THRα1" refers to thyroid hormone receptor alpha isoform 1 and encompasses both human THRα1, as depicted by NCBI accession number NP_955366.1, as well as functionally equivalent THRα1 from other mammalian species and any functionally equivalent isoforms.

The term "THRα2" refers to thyroid hormone receptor alpha isoform 2 and encompasses both human THRα2, as depicted by NCBI accession number NP_001177848.1, as well as functionally equivalent THRα2 from other mammalian species and any functionally equivalent isoforms.

The term "THRα-expressing cancers" refers to cancers which may be characterized at least by an increase of the THRα1 isoform and/or a decrease in the THRα2 isoform. The term "THRα-expressing cancers" also refers to cancers which may be characterized by the expression levels of the THRα1 isoform and/or the THRα2 isoform. The expression levels of the THRα1 isoform and/or the THRα2 isoform is determined, for example, by either the presence of their respective RNA transcripts or proteins determined by a detection method, such as, polymer chain reaction (PCR) or immunohistochemistry (IHC), respectively.

The term "functionally equivalent" as referred to herein is meant to refer to forms of for e.g., THRα1, THRα2, including all mammalian forms from different species, and isoforms or mutants of any of these, that possess the same or similar function and/or activity.

The term "mammal" is used herein to refer to both human and non-human mammals including domestic and animals e.g. cats, dogs, and like, livestock and undomesticated mammals.

The term "biological sample" is meant to encompass any mammalian sample that contains one or more of the thyroid hormone receptors, THRα1 and THRα2, and/or related proteins e.g. related proteins that may be indicative of the levels of THRα1 and/or THRα2. Suitable biological samples include for example, tissue biopsies, blood, serum, plasma or urine. The sample is obtained from the mammal in a manner well-established in the art.

The term "chemotherapy" refers to a treatment for a disease, disorder or condition, such as cancer, that comprises administration of chemical agents that have a specific toxic effect for that disease, disorder or condition. In an embodiment, the chemotherapy works during different phases of the cell cycle, either classified as a cell-cycle specific agent (effective during certain phases of cell cycle) and cell-cycle nonspecific agents (effective during all phases of cell cycle).

The term "endocrine therapy" refers to a treatment for a disease, disorder or condition that comprises administration of agents which slow or stop the growth of hormone-sensitive tumors by blocking the body's ability to produce hormones or by interfering with hormone action.

The term "targeted therapy" refers to a treatment for a disease, disorder or condition that is designed to target cells that are afflicted with the disease, disorder of condition over normal cells. Some targeted therapies block the action of certain enzymes, proteins or other molecules which may be involved in the disease, disorder of condition. Targeted therapies also include therapies which target the delivery of therapeutic agents or substances directly to the targeted cells.

The term "immunotherapy" refers to a treatment for a disease, disorder or condition which comprises administration of agents which induce, enhance or suppress a subject's immune response.

In the context of the above-defined therapies, the term "agent", without further limitation, refers to chemical agents as well as other agents, such as radiation, ultrasound and heat that are used to treat a disease, disorder of condition.

The term "in combination" as used herein refers to an assemblage of agents for use in therapy either by simultaneous, contemporaneous or in sequence administration or use.

Simultaneous administration refers to administration of an admixture (whether a true mixture, a suspension, an emulsion or other physical combination) of all of the agents at the same time. For example, the combination may be an admixture of agents or agents in separate containers that are combined just prior to administration or use.

The term "in sequence" as used herein refers to an order of administration or use wherein one agent is administered or used, for example at least 12-24 hours, and for example more than 18 hours, before or for example 18 hours after, a dose of another agent is administered or used (i.e. not contemporaneously).

The term "contemporaneously" as used in for example "contemporaneous administration" and "administered contemporaneously" means that active agents or therapies are administered to a subject such that they are both biologically active in the subject at the same time. The exact details of the administration will depend on the pharmacokinetics of the two substances in the presence of each other, and can include administering one substance within 12-24 hours of administration of the other, if the pharmacokinetics are suitable. Designs of suitable dosing regimens are routine for one skilled in the art.

II. Methods and Uses of the Application

The present application includes a method of treating a disease, disorder or condition that benefits from inhibition of THRα1, comprising administering an effective amount of one or more compounds of Formula (I), or a pharmaceutically acceptable salt and/or solvate thereof, to a subject in need thereof, wherein the compounds of the Formula (I) are:

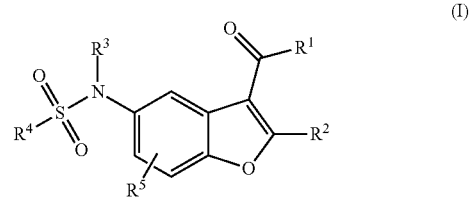

wherein
R[1] is selected from $C_{1-6}$alkyl, $OC_{1-6}$alkylene, $OC_{1-6}$alkylene-$OC_{1-6}$alkyl, $OC_{1-6}$alkylenearyl, OH and unsubstituted or substituted aryl;
the substituents on R[1] are selected from $OC_{1-6}$alkylene-NR[6]R[7] and $OC_{1-6}$alkylene-N(O)R[6]R[7];
R[2] is selected from $C_{1-6}$alkyl, aryl and $C_{1-6}$alkylene-$OC_{1-6}$alkyl;
R[3] is selected from H, $C_{1-6}$alkyl and $SO_2$R[8];
R[4] is selected from $C_{1-6}$alkyl, halo$C_{1-6}$alkyl and unsubstituted or substituted aryl;
the substituents on R[4] are selected from one or more of halo, $C_{1-6}$alkyl, $OC_{1-6}$alkylene, NR[9]C(O)$C_{1-6}$alkyl and COOH;
R[5] is selected from H, halo and $C_{1-6}$alkyl;
R[6], R[7], R[8] and R[9] are independently selected from one or more of H and $C_{1-6}$alkyl; and
one or more available hydrogens are optionally replaced with D and/or F;
or a salt and/or solvate thereof.

In an embodiment, R[1] of the compound of Formula (I) is selected from $C_{1-4}$alkyl, $OC_{1-4}$alkylene, $OC_{1-4}$alkylene-$OC_{1-4}$alkyl, $OC_{1-4}$alkylenearyl, OH and unsubstituted or substituted phenyl wherein the substituents on R[1] are selected from one or two of $OC_{1-4}$alkylene-NR[6]R[7] and $OC_{1-4}$alkylene-N(O)R[6]R[7]. In another embodiment, R[1] is a substituted phenyl wherein the substituents on R[1] are selected from one or two of $OC_{1-4}$alkylene-NR[6]R[7] and $OC_{1-4}$alkylene-N(O)R[6]R[7]. In a further embodiment, R[1] is a substituted phenyl wherein the substituent on R[1] is $OC_{1-4}$alkylene-NR[6]R[7] wherein R[6] and R[7] is $C_{1-6}$alkyl. In yet a further embodiment, R[1] is a substituted phenyl wherein the substituent on R[1] is $OC_{1-4}$alkylene-NR[6]R[7] wherein R[6] and R[7] is $C_{1-4}$alkyl. In yet a further embodiment, R[1] is a substituted phenyl wherein the substituent on R[1] is $OC_{1-4}$alkylene-NR[6]R[7] wherein R[6] and R[7] is selected from methyl, ethyl, propyl and butyl.

In an embodiment, R[2] of the compound of Formula (I) is selected from $C_{1-6}$alkyl, phenyl and $C_{1-4}$alkylene-$OC_{1-4}$alkyl. In another embodiment, R[2] is $C_{1-6}$alkyl. In a further embodiment, R[2] is selected from methyl, ethyl, propyl and butyl. In yet a further embodiment, R[2] is butyl.

In an embodiment, R[3] of the compound of Formula (I) is selected from H and $SO_2$R[8] wherein R[8] is $C_{1-6}$alkyl. In another embodiment, R[3] is selected from H and $SO_2$R[8] wherein R[8] is selected from $C_{1-4}$alkyl. In a further embodiment, R[3] is selected from H and $SO_2$R[8] wherein R[8] is selected from methyl, ethyl, propyl and butyl. In yet a further embodiment, R[3] selected from H and $SO_2$R[8] wherein R[8] is tosyl. In another embodiment, R[3] is H.

In an embodiment, R[4] of the compound of Formula (I) is selected from halo$C_{1-4}$alkyl and unsubstituted or substituted phenyl wherein the substituents on R[4] are selected from one or two of halo, $C_{1-4}$alkyl, $OC_{1-4}$alkylene, NR[9]C(O)$C_{1-4}$alkyl and COOH. In another embodiment, R[4] is selected from $C_{1-4}$alkyl and substituted phenyl wherein the substituents on R[4] are selected from one or two of halo, $C_{1-4}$alkyl, $OC_{1-4}$alkylene, NR[9]C(O)$C_{1-4}$alkyl and COOH. In a further embodiment, R[4] is $C_{1-4}$alkyl. In yet a further embodiment, R[4] is selected from methyl, ethyl, propyl and butyl. In a yet a further embodiment, R[4] is methyl.

In an embodiment, R[5] of the compound of Formula (I) is selected from H, halo and $C_{1-4}$alkyl. In an embodiment, R[5] is H. In an embodiment, R[5] is halo. In another embodiment, R[5] is selected from F, Cl, Br and I. In an embodiment, R[5] is selected from methyl, ethyl, propyl and butyl.

The present application also includes a method of treating a disease, disorder or condition that benefits from inhibition of THRα1, comprising administering an effective amount of one or more compounds of Formula (Ia), or a pharmaceutically acceptable salt and/or solvate thereof, to a subject in need thereof, wherein the compounds of the Formula (Ia) are:

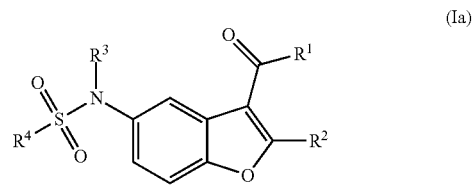

(Ia)

wherein
R[1] is selected from $C_{1-6}$alkyl, halo$C_{1-6}$alkyl, $OC_{1-6}$alkylene, $OC_{1-6}$alkylene-$OC_{1-6}$alkyl, $OC_{1-6}$alkylenearyl, OH and unsubstituted or substituted aryl;
the substituents on R[1] are selected from $OC_{1-6}$alkylene-NR[6]R[7] and $OC_{1-6}$alkylene-N(O)R[6]R[7];
R[2] is selected from $C_{1-6}$alkyl, aryl and $C_{1-6}$alkylene-$OC_{1-6}$ alkyl;
R[3] is selected from H, $C_{1-6}$alkyl and $SO_2$R[8];
R[4] is selected from $C_{1-6}$alkyl, halo$C_{1-6}$alkyl and unsubstituted or substituted aryl;
the substituents on R[4] are selected from one or more of halo, $C_{1-6}$alkyl, $OC_{1-6}$alkylene, NR[9]C(O)$C_{1-6}$alkyl and COOH;
R[6], R[7], R[8] and R[9] are independently selected from one or more of H and $C_{1-6}$alkyl; and
one or more available hydrogens are optionally replaced with D and/or F; or a salt and/or solvate thereof.

In an embodiment, R[1] of the compound of Formula (Ia) is selected from $C_{1-4}$alkyl, $OC_{1-4}$alkylene, $OC_{1-4}$alkylene-$OC_{1-4}$alkyl, $OC_{1-4}$alkylenearyl, OH and unsubstituted or substituted phenyl wherein the substituents on R[1] are selected from one or two of $OC_{1-4}$alkylene-NR[6]R[7] and $OC_{1-4}$alkylene-N(O)R[6]R[7]. In another embodiment, R[1] is a substituted phenyl wherein the substituents on R[1] are selected from one or two of $OC_{1-4}$alkylene-NR[6]R[7] and $OC_{1-4}$alkylene-N(O)R[6]R[7]. In a further embodiment, R[1] is a substituted phenyl wherein the substituent on R[1] is $OC_{1-4}$alkylene-NR[6]R[7] wherein R[6] and R[7] is $C_{1-6}$alkyl. In yet a further embodiment, R[1] is a substituted phenyl wherein the substituent on R[1] is $OC_{1-4}$alkylene-NR[6]R[7] wherein R[6] and R[7] is $C_{1-4}$alkyl. In yet a further embodiment, R[1] is a substituted phenyl wherein the substituent on R[1] is $OC_{1-4}$alkylene-NR[6]R[7] wherein R[6] and R[7] is selected from methyl, ethyl, propyl and butyl.

In an embodiment, R[2] of the compound of Formula (Ia) is selected from $C_{1-6}$alkyl, phenyl and $C_{1-4}$alkylene-$OC_{1-4}$alkyl. In another embodiment, R[2] is $C_{1-6}$alkyl. In a further embodiment, R[2] is selected from methyl, ethyl, propyl and butyl. In yet a further embodiment, R[2] is butyl.

In an embodiment, R[3] of the compound of Formula (Ia) is selected from H and $SO_2$R[8] wherein R[8] is $C_{1-6}$alkyl. In another embodiment, R[3] is selected from H and $SO_2$R[8] wherein R[8] is selected from $C_{1-4}$alkyl. In a further embodiment, R[3] is selected from H and $SO_2$R[8] wherein R[8] is selected from methyl, ethyl, propyl and butyl. In yet a further embodiment, R[3] selected from H and $SO_2$R[8] wherein R[8] is tosyl. In another embodiment, R[3] is H.

In an embodiment, R⁴ of the compound of Formula (Ia) is selected from $C_{1-4}$alkyl, halo$C_{1-4}$alkyl and unsubstituted or substituted phenyl wherein the substituents on R⁴ are selected from one or two of halo, $C_{1-4}$alkyl, $OC_{1-4}$alkylene, $NR^9C(O)C_{1-4}$alkyl and COOH. In another embodiment, R⁴ is selected from $C_{1-4}$alkyl and substituted phenyl wherein the substituents on R⁴ are selected from one or two of halo, $C_{1-4}$alkyl, $OC_{1-4}$alkylene, $NR^9C(O)C_{1-4}$alkyl and COOH. In a further embodiment, R⁴ is $C_{1-4}$alkyl. In yet a further embodiment, R⁴ is selected from methyl, ethyl, propyl and butyl. In a yet a further embodiment, R⁴ is methyl.

In an embodiment, the compound of Formula (I) or the compound of Formula (Ia) is selected from one of the following compounds, including pharmaceutically acceptable salts and/or solvates thereof:

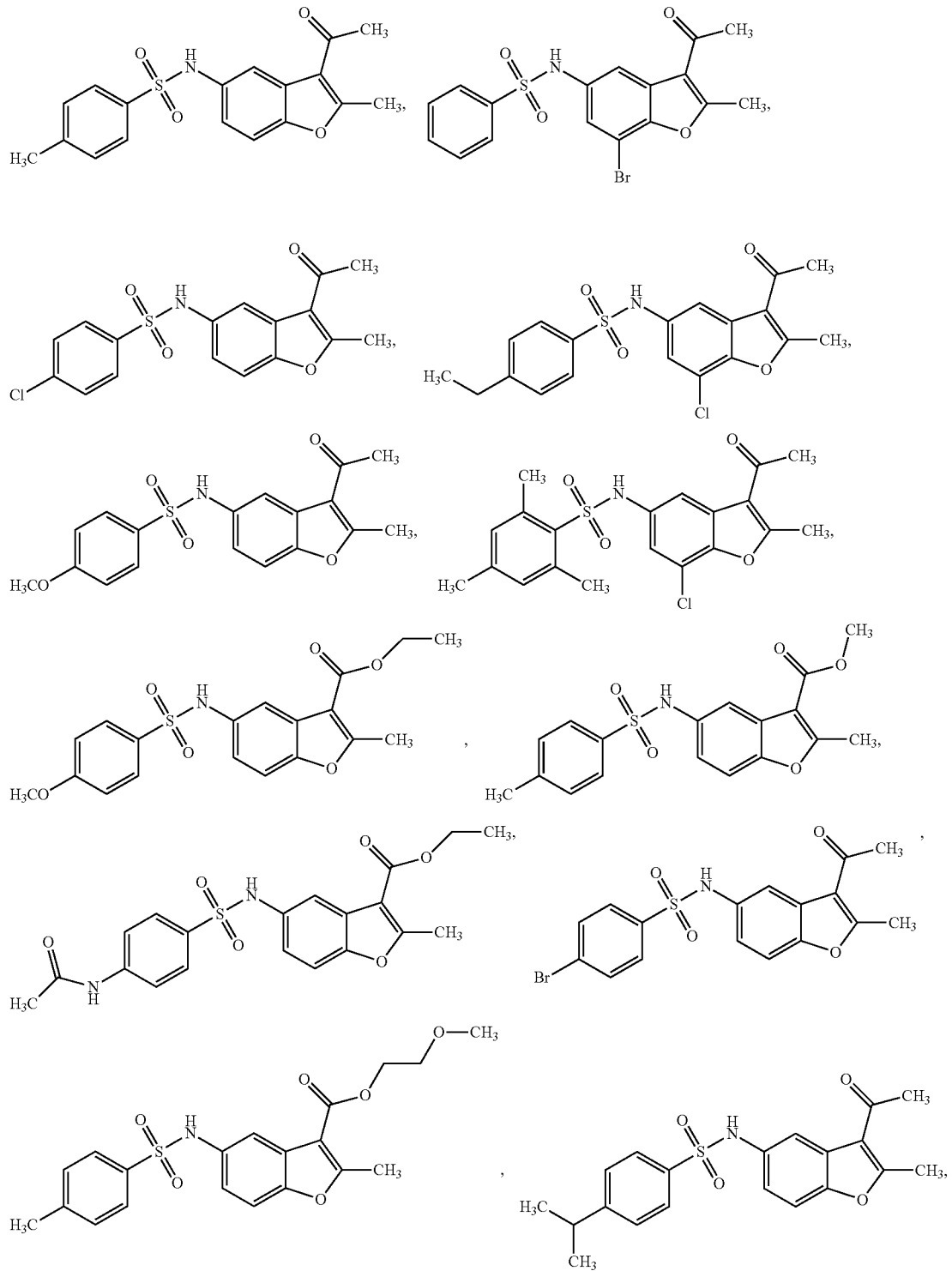

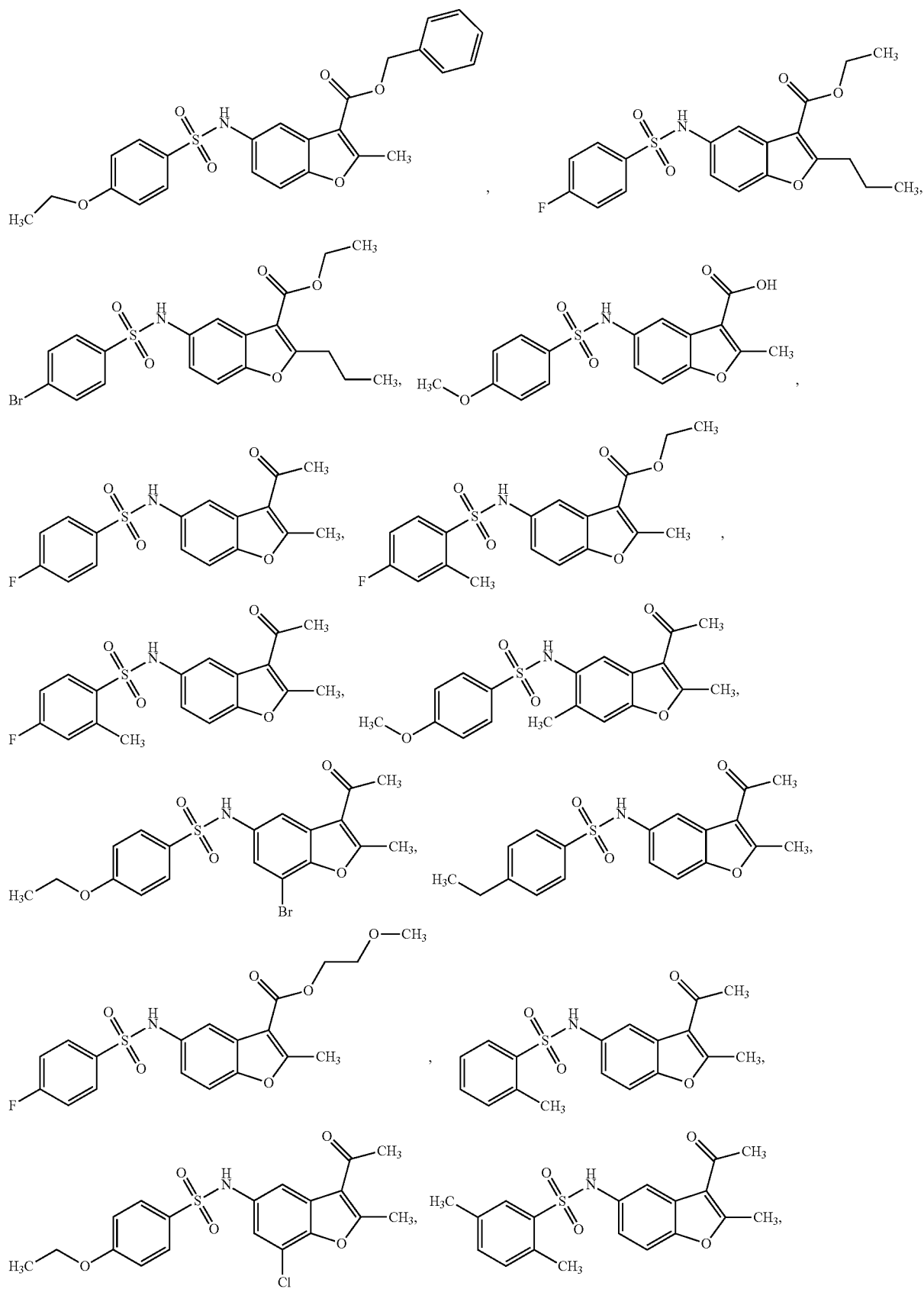

-continued
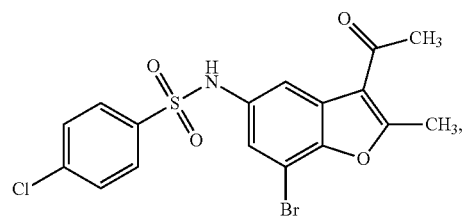
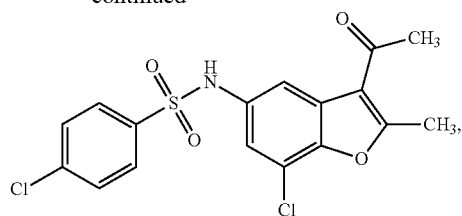
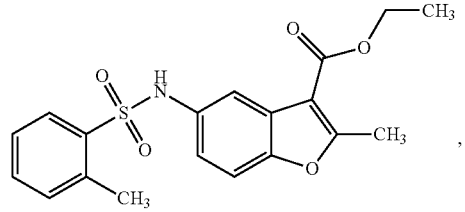
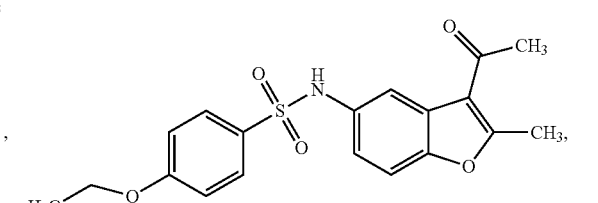
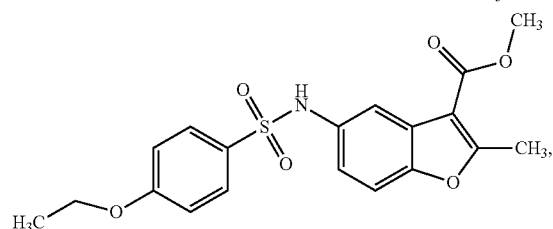
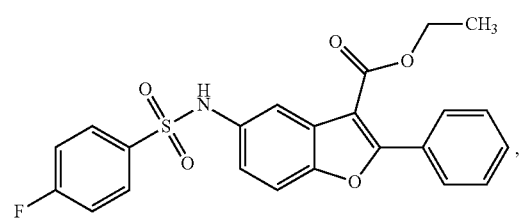
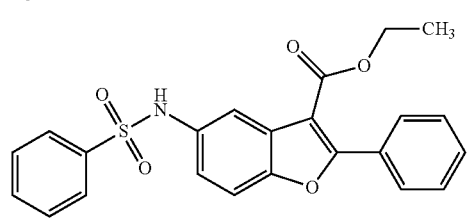
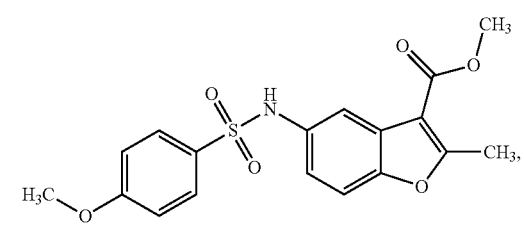
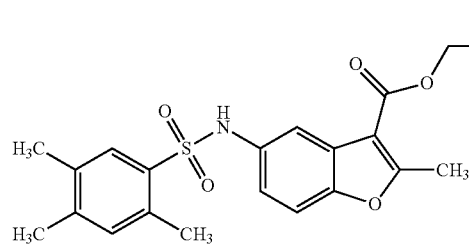
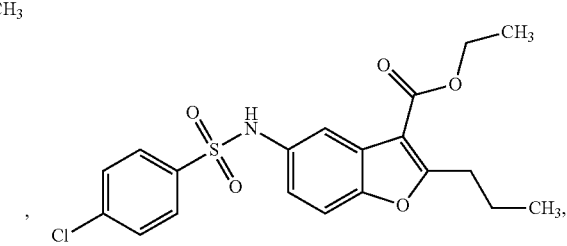
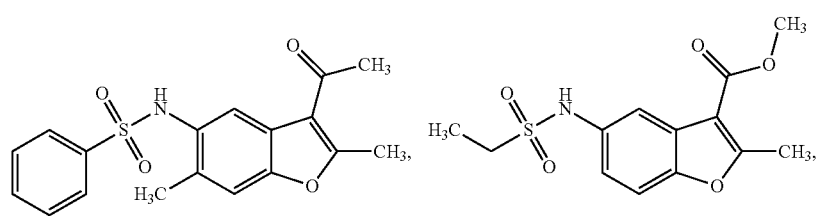
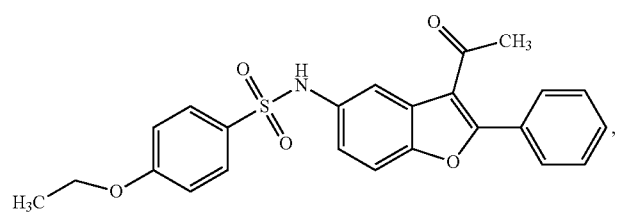
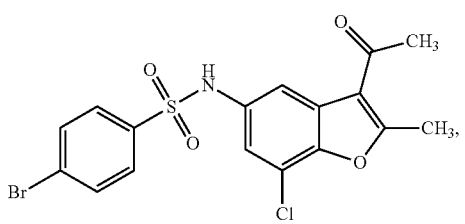

-continued
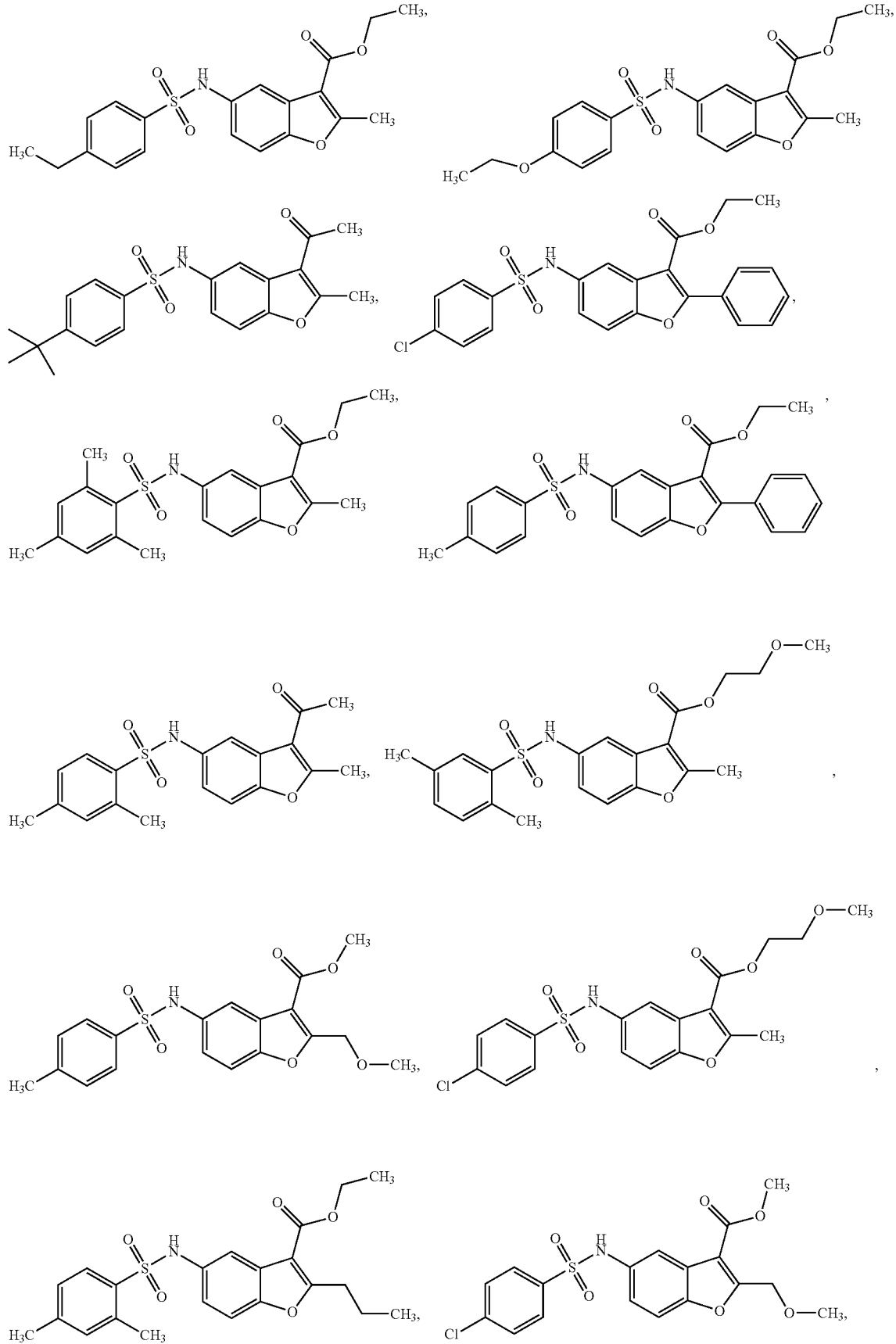

-continued
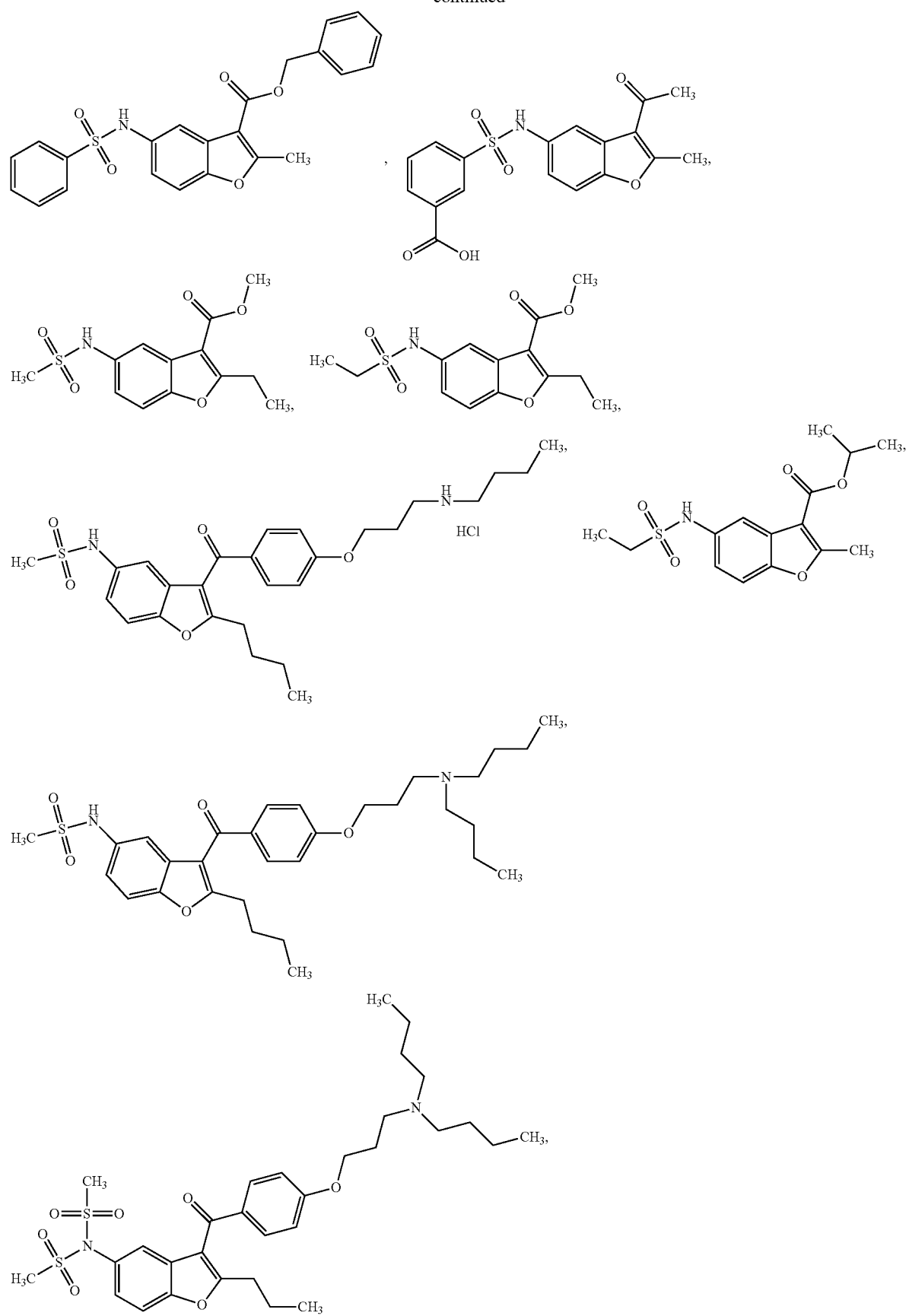

-continued

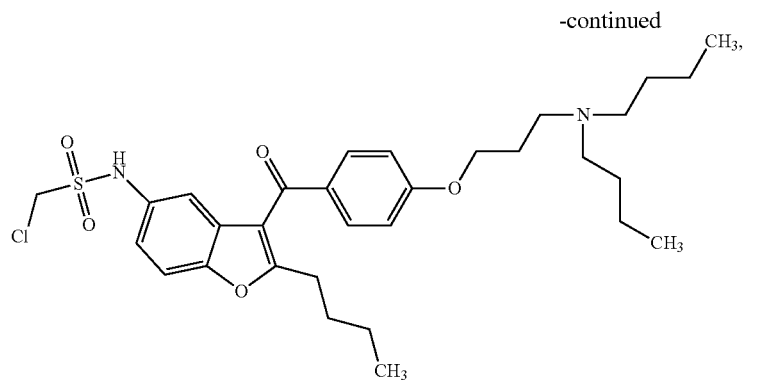

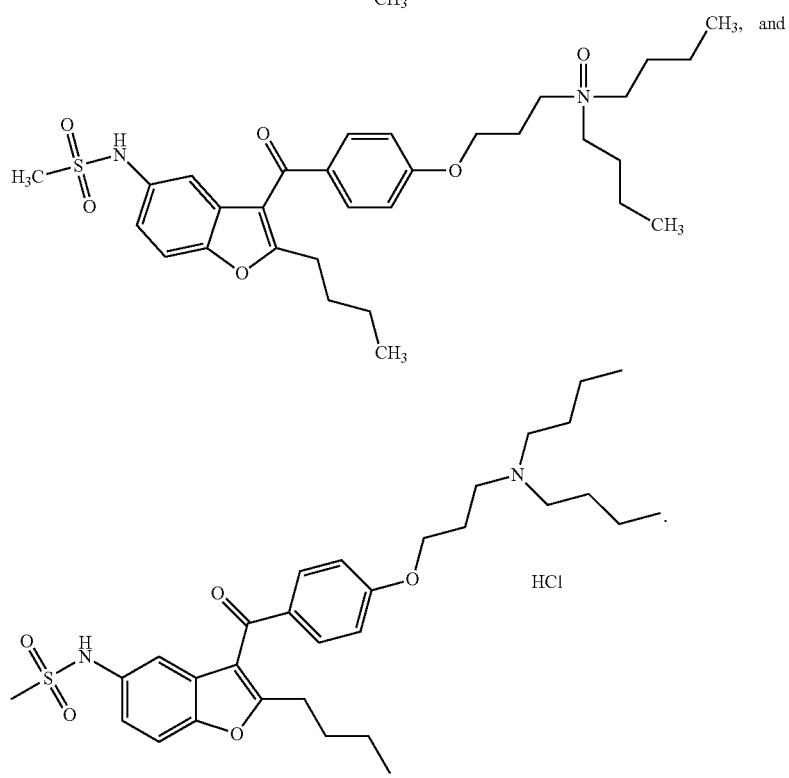

In an embodiment, the compound of Formula (I) or the compound of Formula (Ia) is dronedarone, or a pharmaceutically acceptable salt and/or solvate thereof. Dronedarone has the following chemical structure:

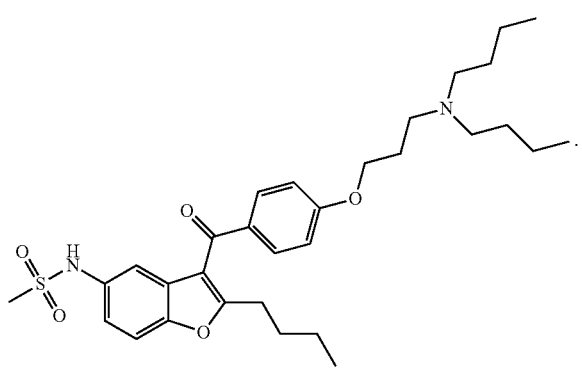 [SMILES: CCCCc1oc2ccc(NS(C)(=O)=O)cc2c1C(=O)c1ccc(OCCCN(CCCC)CCCC)cc1]

A person skilled in the art would appreciate that this compound may form a pharmaceutically acceptable acid addition salt of the tertiary amine. In some embodiments, the pharmaceutically acceptable acid addition salt is the hydrochloride salt.

The present application also includes a use of one or more compounds of Formula (I) or one or more compounds of Formula (Ia), or a pharmaceutically acceptable salt and/or solvate thereof, for treating a disease, disorder or condition that benefits from inhibition of THRα1, as well as a use of one or more compounds of Formula (I) or one or more compounds of Formula (Ia), or a pharmaceutically acceptable salt and/or solvate thereof, for preparation of a medicament for treating a disease, disorder or condition that benefits from inhibition of THRα1. Also included in the present application is one or more compounds of Formula (I) or one or more compounds of Formula (Ia), or a pharmaceutically acceptable salt and/or solvate thereof, for use to treat a disease, disorder or condition that benefits from inhibition of THRα1.

In another aspect of the application there is included method of treating a disease, disorder or condition that benefits from inhibition of THRα1 comprising administering, to a subject in need thereof, one or more compounds of Formula (I) or one or more compounds of Formula (Ia), or a pharmaceutically acceptable salt and/or solvate thereof, in combination with one or more other therapies for treating the disease, disorder or condition that benefits from inhibition of THRα1.

In another aspect of the application there is included a use of one or more compounds of Formula (I), or one or more compounds of Formula (Ia), or a pharmaceutically acceptable salt and/or solvate thereof, in combination with one or more other therapies for treating a disease, disorder or condition that benefits from inhibition of THRα1, to treat the disease, disorder or condition that benefits from inhibition of THRα1. In another aspect of the application there is included one or more compounds of Formula (I), or one or more compounds of Formula (Ia), or a pharmaceutically acceptable salt and/or solvate thereof, for preparation of a medicament to use in combination with one or more other therapies for treating a disease, disorder or condition that benefits from inhibition of THRα1, to treat the disease, disorder or condition that benefits from inhibition of THRα1.

In another aspect of the application there is included a pharmaceutical composition for treating a disease, disorder or condition that benefits from inhibition of THRα1 comprising one or more compounds of Formula (I) or one or more compounds of Formula (Ia), or a pharmaceutically acceptable salt and/or solvate thereof, in combination with one or more other therapies for treating the disease, disorder or condition that benefits from inhibition of THRα1, and a pharmaceutically acceptable carrier and/or diluent.

The present application also includes a method of treating a disease, disorder or condition that benefits from the upregulation of THRα2, comprising administering an effective amount of one or more compounds of Formula (II), or a pharmaceutically acceptable salt and/or solvate thereof, to a subject in need thereof, wherein the compounds of Formula (II) are:

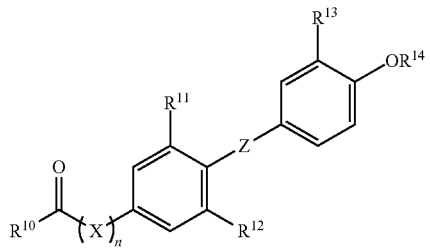

wherein
$R^{10}$ is selected from OH, $C_{1-6}$alkyl, $OC_{1-6}$alkyl and halo$C_{1-6}$alkyl;
$R^{11}$, $R^{12}$ and $R^{13}$ are independently selected from H, halo, $C_{1-6}$alkyl and $OC_{1-6}$alkyl;
$R^{14}$ is selected from H, halo and $C_{1-6}$alkyl;
X is selected from NH, O, $C_{1-6}$alkylene, $OC_{1-6}$alkylene and $C_{1-6}$alkylene-O;
n is 1 or 2;
Z is selected from NH, O and $C_{1-6}$alkylene; and
one or more available hydrogens are optionally replaced with D and/or F;
or a salt and/or solvate thereof;
with proviso that when X is O, n is not 2.

In an embodiment, $R^{10}$ of compound of Formula (II) is selected from OH and $C_{1-4}$alkyl. In another embodiment, $R^{10}$ is OH. In a further embodiment, $R^{10}$ is $C_{1-4}$ alkyl. In yet a further embodiment, $R^{10}$ is selected from methyl, ethyl, propyl and butyl. In yet a further embodiment, $R^{10}$ is methyl.

In an embodiment, $R^{11}$, $R^{12}$ and $R^{13}$ of compound of Formula (II) are independently selected from halo and $C_{1-4}$alkyl. In another embodiment, $R^{11}$, $R^{12}$ and $R^{13}$ are halo. In a further embodiment, $R^{11}$, $R^{12}$ and $R^{13}$ are selected from F, Cl, Br and I. In another embodiment, $R^{11}$, $R^{12}$ and $R^{13}$ are $C_{1-4}$alkyl. In a further embodiment, $R^{11}$, $R^{12}$ and $R^{13}$ are selected from methyl, ethyl, propyl, isopropyl, butyl, t-butyl and sec-butyl. In yet a further embodiment, $R^{11}$, $R^{12}$ and $R^{13}$ are selected from methyl and isopropyl.

In an embodiment, $R^{14}$ of the compound of Formula (II) is selected from H and $C_{1-6}$alkyl. In another embodiment, $R^{14}$ is $C_{1-6}$alkyl. In a further embodiment, $R^{14}$ is selected from methyl, ethyl and propyl. In yet a further embodiment, $R^{14}$ is methyl. In another embodiment, $R^{14}$ is H.

In an embodiment, X of the compound of Formula (II) is selected from O, $OC_{1-6}$alkylene and $C_{1-6}$alkylene-O. In another embodiment, X is selected from O, $OC_{1-4}$alkylene and $C_{1-4}$alkylene-O. In a further embodiment, X is O. In another embodiment, X is $C_{1-4}$alkylene-O.

In an embodiment, Z of the compound of Formula (II) is selected from O and $C_{1-6}$alkylene. In another embodiment, Z is selected from O and $C_{1-4}$alkylene. In an embodiment, Z is O. In another embodiment, Z is $C_{1-4}$alkylene. In a further embodiment, Z is selected from methylene, ethylene and propylene. In yet a further embodiment, Z is methylene.

In an embodiment, the compound of Formula (II) is selected from:

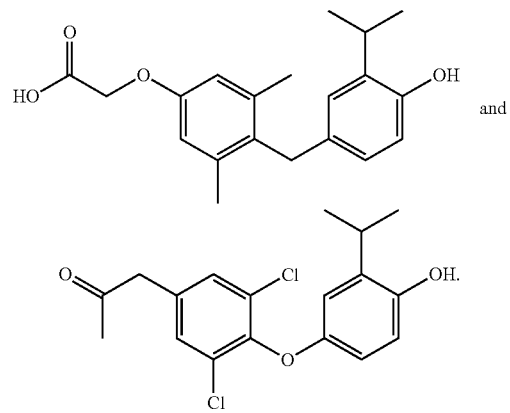

The present application also includes a use of one or more compounds of Formula (II), or a pharmaceutically acceptable salt and/or solvate thereof, for treating a disease, disorder or condition that benefits from the upregulation of THRα2, as well as a use of one or more compounds of Formula (II), or a pharmaceutically acceptable salt and/or solvate thereof, for preparation of a medicament for treating a disease, disorder or condition that benefits from the upregulation of THRα2. Also included in the present application is a compound of Formula (II), or a pharmaceutically acceptable salt and/or solvate therefore, for use to treat a disease, disorder or condition that benefits from the upregulation of THRα2.

In another aspect of the application there is included a method of treating a disease, disorder or condition that benefits from the upregulation of THRα2 comprising administering, to a subject in need thereof, one or more compounds of Formula (II), or a pharmaceutically acceptable salt and/or solvate thereof, in combination with one or more other therapies for the treating disease, disorder or condition that benefits from the upregulation of THRα2.

In another aspect of the application there is included a use of one or more compounds of Formula (II), or a pharmaceutically acceptable salt and/or solvate thereof, in combination with one or more other therapies for treating a disease, disorder or condition that benefits from upregulation of THRα2, to treat the disease, disorder or condition that benefits from upregulation of THRα2. In another aspect of the application there is included one or more compounds of Formula (II), or a pharmaceutically acceptable salt and/or solvate thereof, for preparation of a medicament to use in combination with one or more other therapies for treating a disease, disorder or condition that benefits from upregulation of THRα2, to treat the disease, disorder or condition that benefits from upregulation of THRα2.

In another aspect of the application there is included a pharmaceutical composition for treating a disease, disorder or condition that benefits from upregulation of THRα2 comprising one or more compounds of Formula (II), or a pharmaceutically acceptable salt and/or solvate thereof, in combination with one or more other therapies for treating the disease, disorder or condition that benefits from upregulation of THRα2, and a pharmaceutically acceptable carrier and/or diluent.

In some embodiments, the disease, disorder or condition that benefits from inhibition of THRα1 and/or upregulation of THRα2 is a cell proliferative disorder. In some embodiments, the disease, disorder or condition that benefits from inhibition of THRα1 and/or upregulation of THRα2, is a THRα-expressing cancer. In another embodiment, the THRα-expressing cancer is selected from breast cancer, nasopharyngeal cancer, renal cancer, gastric cancer, pancreatic cancer, uterine cancer, cervical cancer, bladder cancer, non-small cell lung cancer, small cell lung cancer, melanoma, colorectal cancer, esophageal cancer, prostate cancer, sarcoma, glioblastoma multiforme (GBM), thyroid cancer, acute myeloid leukemia (AML), acute lymphocytic leukemia (ALL), lymphoma and ovarian cancer. In some embodiments, the cancer is breast cancer.

In some embodiments, the one or more other therapies for treating the disease, disorder or condition that benefits from inhibition of THRα1 and/or upregulation of THRα2 is a chemotherapy. In some embodiments, the one or more other therapies for treating the disease, disorder or condition that benefits from inhibition of THRα1 and/or upregulation of THRα2 is a cancer chemotherapy. In some embodiments, the one or more other therapies for treating the disease, disorder or condition that benefits from inhibition of THRα1 and/or upregulation of THRα2 is a THR-expressing cancer chemotherapy In some embodiments, the chemotherapy comprises administering to the subject, or using, one or more chemical agents selected from an alkylating agent, antimetabolite, anthracycline, antitumor antibiotic, monoclonal antibody, platinum-based derivative, anti-HER2 compounds and plant alkaloid. In some embodiments, the one or more chemical agents are selected from docetaxel, doxorubicin, epirubicin, abraxane, paclitaxel, eribulin, capecitabine, hereceptin, perfuzumab, trastuzumab emtansin (T-DM1) and vinorelbine.

In some embodiments, the one or more therapies for treating the disease, disorder or condition that benefits from inhibition of THRα1 and/or upregulation of THRα2 are selected from an endocrine therapy, a targeted therapy and an immunotherapy.

In some embodiments, the endocrine therapy comprises administering one or more agents selected from tamoxifen, letrozole, anastrozole, fulvestrant and exemestane.

In some embodiments, the targeted therapy is an anti-HER2 therapy. In some embodiments, the anti-HER2 therapy comprises administering one or more agents selected from TDM1, herceptin and pertuzumab.

In some embodiments, the immunotherapy comprises administering one or more agents selected from PDL1/PD1 inhibitors and CTLA4 antagonists. In some embodiments, the PDL1/PD1 inhibitor is nivolumab. In some embodiments, the CTLA4 antagonist is ipilumumab. In some embodiments, the one or more agents for immunotherapy are selected from cell-based immunotherapies such as immune effector cells, granulocyte colony-stimulating factor (G-CSF), interferons, imiquimod, cellular membrane fractions from bacteria, chemokines, synthetic cytosine phosphate-guanosine (CpG), oligodeoxynucleotides and glucans.

In a further aspect of the present application includes a method for treating breast cancer through the induction of hypothyroidism. In an embodiment, the method comprises inhibiting THRα1 expression and/or inducing THRα2 expression.

In another aspect of the present application includes a method of inhibiting THRα1 comprising administering an effective amount of one or more compounds of Formula (I) or one or more compounds of Formula (Ia) as defined above, or a pharmaceutically acceptable salt, and/or solvate thereof, to a subject in need thereof.

In another aspect of the present application includes a method of upregulating THRα2 comprising administering an effective amount of one or more compounds of Formula (II) as defined above, or a pharmaceutically acceptable salt, and/or solvate thereof, to a subject in need thereof.

In another aspect of the present application includes a method of treating a disease, disorder or condition that benefits from inhibition of THRα1 and/or upregulation of THRα2 comprising administering an effective amount of a compound of Formula (I) or a compound of Formula (Ia) as defined above, or a salt and/or solvate thereof, and an effective amount of a compound of Formula (II) as defined above, or a salt and/or solvate thereof, to the subject.

In another aspect, the present application includes a compound of Formula (I) or a compound Formula (Ia), or a salt and/or solvate thereof, in combination with a compound of Formula (II), for treating a disease, disorder or condition that benefits from the inhibition of THRα1 and/or upregulation of THRα2. The present application also includes a use of a compound of Formula (I) or a compound of Formula (Ia) as defined above, or a salt and/or solvate thereof, in combination with a compound of Formula (II) as defined above, or a salt and/or solvate thereof, to treat a disease, disorder or condition that benefits from the inhibition of THRα1 and/or upregulation of THRα2. The present application also includes a use of a compound of Formula (I) or a compound of Formula (Ia) as defined above, or a salt and/or solvate thereof, in combination with a compound of Formula (II) as defined above, or a salt and/or solvate thereof, to prepare a medicament to treat a disease, disorder or condition that benefits from the inhibition of THRα1 and/or upregulation of THRα2. In some embodiments, the compound of Formula (I) or compound of Formula (Ia) as defined above, or a salt and/or solvate thereof, in combination with a compound of Formula (II) as defined above, or a salt and/or solvate thereof, are administered, or are used in combination with one or more other therapies for treating a disease, disorder or condition that benefits from the inhibition of THRα1 and/or upregulation of THRα2.

In some embodiments, the disease, disorder or condition that benefits from inhibition of THRα1 and/or upregulation of THRα2 is a cell proliferative disorder. In some embodiments, the disease, disorder or condition that benefits from inhibition of THRα1 and/or upregulation of THRα2, is a THRα-expressing cancer. In another embodiment, the THRα-expressing cancer is selected from breast cancer, nasopharyngeal cancer, renal cancer, gastric cancer, pancreatic cancer, uterine cancer, cervical cancer, bladder cancer, non-small cell lung cancer, small cell lung cancer, melanoma, colorectal cancer, esophageal cancer, prostate cancer, sarcoma, glioblastoma multiforme (GBM), thyroid cancer, acute myeloid leukemia (AML), acute lymphocytic leukemia (ALL), lymphoma and ovarian cancer. In some embodiments, the cancer is breast cancer.

A further aspect of the present application includes a method of treating a subject having a THRα-expressing cancer comprising administering an effective amount of a compound of Formula (I) or a compound of Formula (Ia) as defined above, or a salt and/or solvate thereof, and an effective amount of a compound of Formula (II) as defined above, or a salt and/or solvate thereof, to the subject.

In a further aspect, the present application includes a compound of Formula (I) or a compound Formula (Ia), or a salt and/or solvate thereof, in combination with a compound of Formula (II), for treating a subject having a THRα-expressing cancer. The present application also includes a use of a compound of Formula (I) or a compound of Formula (Ia) as defined above, or a salt and/or solvate thereof, in combination with a compound of Formula (II) as defined above, or a salt and/or solvate thereof, to treat a subject having a THRα-expressing cancer. The present application also includes a use of a compound of Formula (I) or a compound of Formula (Ia) as defined above, or a salt and/or solvate thereof, in combination with a compound of Formula (II) as defined above, or a salt and/or solvate thereof, to prepare a medicament to treat a subject having a THRα-expressing cancer. In some embodiments, the compound of Formula (I) or compound of Formula (Ia) as defined above, or a salt and/or solvate thereof, in combination with a compound of Formula (II) as defined above, or a salt and/or solvate thereof, are administered, or are used in combination with one or more other therapies for treating a subject having a THRα-expressing cancer.

In another aspect of the present application, the one or more compounds of Formula (I), (Ia) and/or (II), and pharmaceutically acceptable salts, and/or solvates thereof, are suitable formulated into pharmaceutical compositions for administration into a subject thereof. Accordingly, the present application further includes a pharmaceutical composition comprising one or more compounds of Formula (I), (Ia) and/or (II) as defined above, or a pharmaceutically acceptable salt, and/or solvate thereof, and a pharmaceutically acceptable carrier and/or diluent.

The present application also includes a method for predicting the therapeutic outcome of subjects having a THRα-expressing cancer comprising measuring the expression of THRα2 and THRα1 transcript variants in biological samples from the subjects, wherein an increase in THRα2 transcript variants and/or a decrease in THRα1 transcript variants compared to controls is predictive of a positive therapeutic outcome and a decrease in THRα2 transcript variants and/or an increase in THRα1 transcript variants compared to controls is predictive of a negative therapeutic outcome. In an embodiment the method further comprises treating subjects with a decrease in THRα2 transcript variants and/or an increase in THRα1 transcript variants compared to controls, identified using the method, with one or more compounds of the application.

The compounds of Formula (I), compounds of Formula (Ia) and compounds of the Formula (II) are either commercially available or may be prepared using methods known in the art. In an embodiment, compounds of Formula (I) and compounds of Formula (Ia) are prepared based on the methods disclosed in WO 2012/032545 and Han et al., Chem. Pharm. Bull (Tokoyo), 2015, 63:295-299. In an embodiment, compounds of Formula (II) are prepared based on the methods disclosed in U.S. Pat. No. 5,883,294 and WO2004/089470.

III. Examples

The following non-limiting examples are illustrative of the present application:

Example 1: Surveying THRα1 and THRα2 Expression Levels Associated with Clinical Outcomes Using a Historical Cohort of Breast Cancer Patients Cohort #1

The study population consisted of 130 patients with invasive breast carcinoma for whom adequate paraffin-embedded tissue was available from the pathology archive of Hamilton Health Sciences (HHS). A list of all patients having a mastectomy or segmental breast resection for primary breast cancer for the year 2007 was generated. The year 2007 was chosen to allow for a minimum of 5 years clinical follow-up. All were pathologically proven primary invasive carcinomas of the breast that measured at least 1 cm in diameter. Patients were excluded if they were treated with neo-adjuvant chemotherapy, if their tumors were multifocal, if their medical history was not available, if inadequate tissue was available to build a tissue microarray (TMA) or if they were known to harbor a BRCA mutation.

Cohort #2

The study population consisted of 158 women with invasive breast carcinoma treated with mastectomy or segmental resection between November 2002 and September 2009. Tumors with adequate paraffin-embedded tissue were selected from the pathology archive of Hamilton Health Sciences (HHS) and confirmed to be primary invasive carcinomas of the breast by a licensed pathologist. Patients were excluded if their tumors were less than 1 cm in size or multifocal, if their medical history was not available or if they were treated with neo-adjuvant chemotherapy.

Clinical Information and Tumor Pathology

Clinical and patient characteristics, including age at diagnosis, treatments received (including the use of thyroid hormone supplementation) and clinical outcomes were extracted from clinical charts and electronic patient records. Tumor pathological parameters, including tumor size, grade, presence or absence of lymphovascular space invasion (LVI), nodal status, stage, estrogen (ER), progesterone (PR) and HER2 status were extracted from the surgical pathology report.

TMA Construction

A representative block of invasive tumor was selected for each patient from the pathology archive. A hematoxylin and eosin (H&E) stained section of each tumor block received was prepared to confirm the diagnosis and to circle the area of invasive tumor with permanent ink for TMA construction. Three 0.6 mm cores of tissue were taken from the paraffin tumor block and used for TMA construction.

Immunohistochemistry

Figure 3:
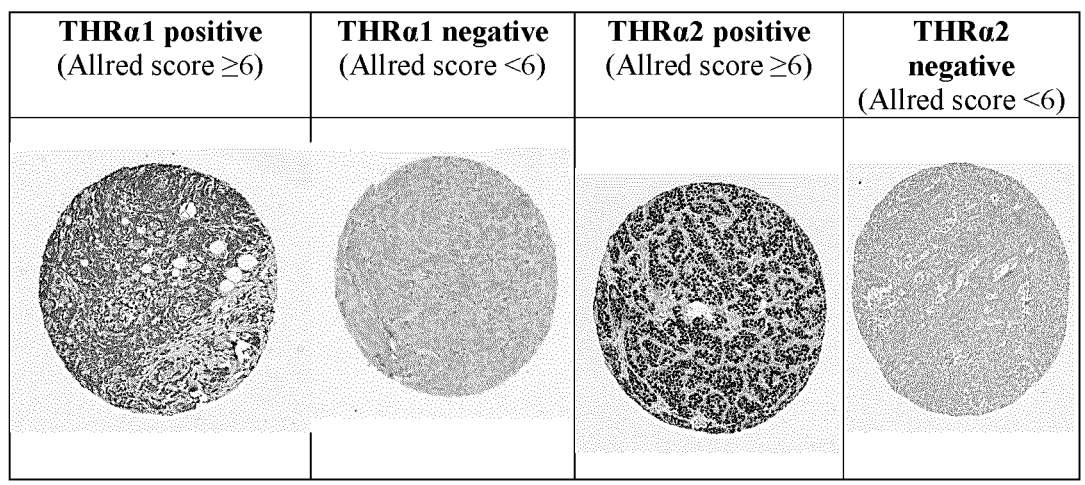
FIG. 3 shows representative immunohistochemical staining of thyroid hormone receptors in breast cancer.

Four micron sections from each tumor block were cut and immunohistochemical staining for THRα1 [Polyclonal rabbit antibody (ab53729), from Abcam plc] and THRα2 [Monoclonal mouse antibody (MA1-4676), from Thermo Fisher Scientific Co] was performed. Microwave antigen retrieval was carried out in a Micromed T/T Mega Microwave Processing Lab Station (ESBE Scientific, Markham, Ontario, Canada). Sections were developed with diaminobenzidine tetrahydrochloride (DAB) and counterstained in Mayer's hematoxylin. Representative tumor samples are illustrated in FIG. 3.

Allred's method [10] was adapted to score each of the immuohistochemical TMA stained sections for THRα1 and THRα2; scores for the intensity of staining (absent: 0, weak: 1, moderate: 2, and strong: 3) were added to the percentage of cells stained (none: 0, <1%: 1, 1-10%: 2, 11-33%: 3, 34-66%: 4 and 67-100%: 5) to yield a 'raw' score of 0 or 2-8. Each tumor was scored in triplicate and the Allred score was averaged among three samples. Both the score and cellular location of expression (nuclear or cytoplasmic) were recorded for each antibody in every tumor.

Statistical Analysis

Patient and tumor characteristics were described using summary statistics. Normality assumptions for continuous factors were assessed visually and highly non-normal factors were transformed using a log-transformation. The Kaplan-Meier method was used to estimate time-to-event outcomes. Overall survival was defined from the date of diagnosis to the date of death; recurrence-free survival was defined from the date of diagnosis to clinical recurrence or death due to any cause. Patients were censored for overall survival and recurrence-free survival at the last date the patient was documented to be alive and recurrence free.

Cox proportional hazards regression was used to investigate the prognostic ability of each factor in univariable analyses. A multivariable model was constructed using forward stepwise selection with selection criteria set at α=0.05 level. Associations between THRα1, THRα2 and other variables were assessed using Spearman rank correlation coefficients (ρ); ρ<|0.30| was considered to be a weak/no association, |0.30|<ρ<|0.70| was considered to be a moderate association, and ρ>|0.70| was considered to be a strong association. Associations between categorical factors and THRs (THRα1 and THRα2) was assessed using two-sample t-tests. An optimal cutpoint of THRα1 and THRα2 was performed by visual examination of Martingale residual plots and $\chi^2$ log-rank test statistics over a range of possible cutpoints. Statistical significance was defined as a p-value <0.05 and all tests were two-sided.

This study was approved by the Hamilton Integrated Research Ethics Board.

Results

Population Characteristics—Cohort #1

Among this cohort of 130 women with breast cancer, the mean age at diagnosis was 65 years. The majority of patients had T1c (31%) or T2 (56%) disease, and 45% had lymph node involvement. Seventy three percent of tumors were ER positive (≥5% staining on IHC), 13% were HER2 positive (3+ IHC, or 2+ IHC and positive fluorescence in situ hybridization) and 21% were triple negative (Table 1). Treatment details were available for 124 patients. Sixteen percent (n=21) did not receive any therapy other than surgery. Treatment consisted of chemotherapy alone in 19% of patients (n=24), hormonal therapy alone in 35% of patients (n=43), and a combination of both chemotherapy and hormonal therapy in 28% of patients (n=35). Forty seven percent (n=61) of patients received adjuvant radiotherapy; for eight of these patients, radiation was the only mode of adjuvant therapy. Twenty-eight patients had a recurrence, resulting in a 5-year recurrence-free survival rate of 74.0% (95% CI 65.3-80.9). The 5-year mortality was 17.7% (95% CI 11.9-26.0).

Population Characteristics—Cohort #2

The mean age of patients at diagnosis was 61 years; 88% had stage 1 or 2 disease (n=135), 23% had lymph node involvement (n=33) and 77% of tumors (n=122) were classified as grade 3 (Table 1b). Treatment consisted of chemotherapy alone in 20% of patients (n=31), radiation alone in 12% (n=18), or a combination of both chemotherapy and radiation in 56% of patients (n=85). Twelve percent of patients (n=19) did not receive any adjuvant treatment. The 5-year OS was 80.6% (95% CI 72.6%-86.5%) and the 5-year recurrence-free survival (RFS) was 73.7% (95% CI 65.2%-80.4%).

Figure 4:
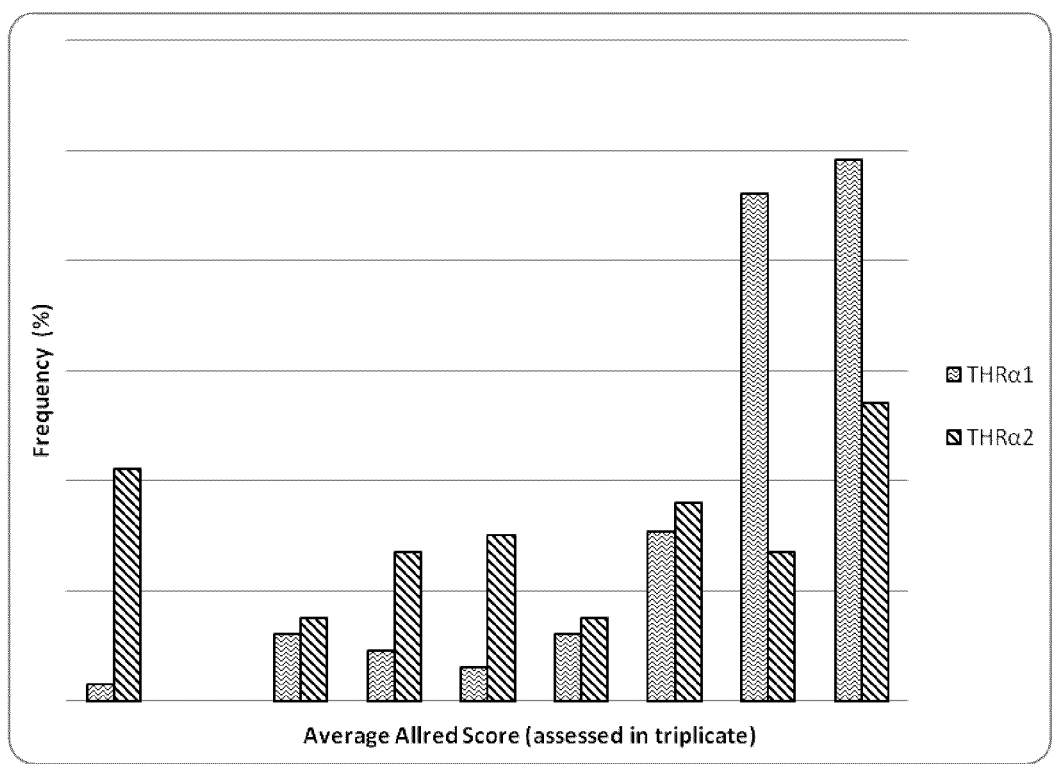
FIG. 4 shows the pattern of expression of THRα1 and THRα2 in a cohort of 130 breast cancer patients. THRα1 was highly expressed (Allred score ≥6) in a high proportion (74%) of assessed breast cancers. THRα2 was highly expressed in 40% of assessed breast tumors.

THRα1 Results:

Among patients in Cohort #1, the median expression level of THRα1 (based on the Allred score) was 7, with a range from 0 to 8 (FIG. 4). When assessed as a continuous variable, THRα1 expression was not associated with age, grade, LVI, tumor size, lymph node involvement or stage of disease. No optimal cutpoint for THRα1 was identified, thus, an Allred score of 6 or higher was arbitrarily deemed to indicate high expression of THRα1, with high nuclear expression in the 74% of tumors. The frequency of high expression was similar for ER positive tumors (75%), HER2 positive tumors (71%) and triple negative tumors (71%). Using neither dichotomized data (high versus low expression) nor continuous data (expression rated according to the Allred score) was there a significant association observed between THRα1 expression and either recurrence-free survival (Table 3a) or overall survival (Table 4a).

Among patients in Cohort #2, the median expression level of THRα1 was 7, with a range from 3 to 8. Using an Allred score of 5 or higher as a cutpoint, THRα1 was expressed in 93% of patients (n=142). THRα1 expression was only weakly/not (Spearman ρ<|0.30|) associated with age, tumor size and stage of disease; no significant association with grade, LVI, or lymph node involvement was observed (p>0.05 for each test). Further, no significant prognostic ability of THRα1 expression was observed for either RFS (HR=0.86, 95% CI=0.63 to 1.16, p=0.31) or OS (HR=0.86, 95% CI=0.62 to 1.18, p=0.34), see Tables 3b and 4b.

THRα2 Results:

Among patients in Cohort #1, the median expression of THRα2 based on the Allred score was 5, with a range of 0 to 8 (FIG. 4). THRα2 was highly expressed (Allred score ≥6) in the nuclei of 40% of tumors but this varied by phenotype. THRα2 was expressed at a high level in 51% of ER positive tumors (40/78), in 6% of HER2 positive tumors (1/17) and in 14% of triple negative (4/28) tumors. There was no significant association observed between THRα2 expression and tumor size, nodal status, disease stage, grade or the presence of LVI.

Figure 5:
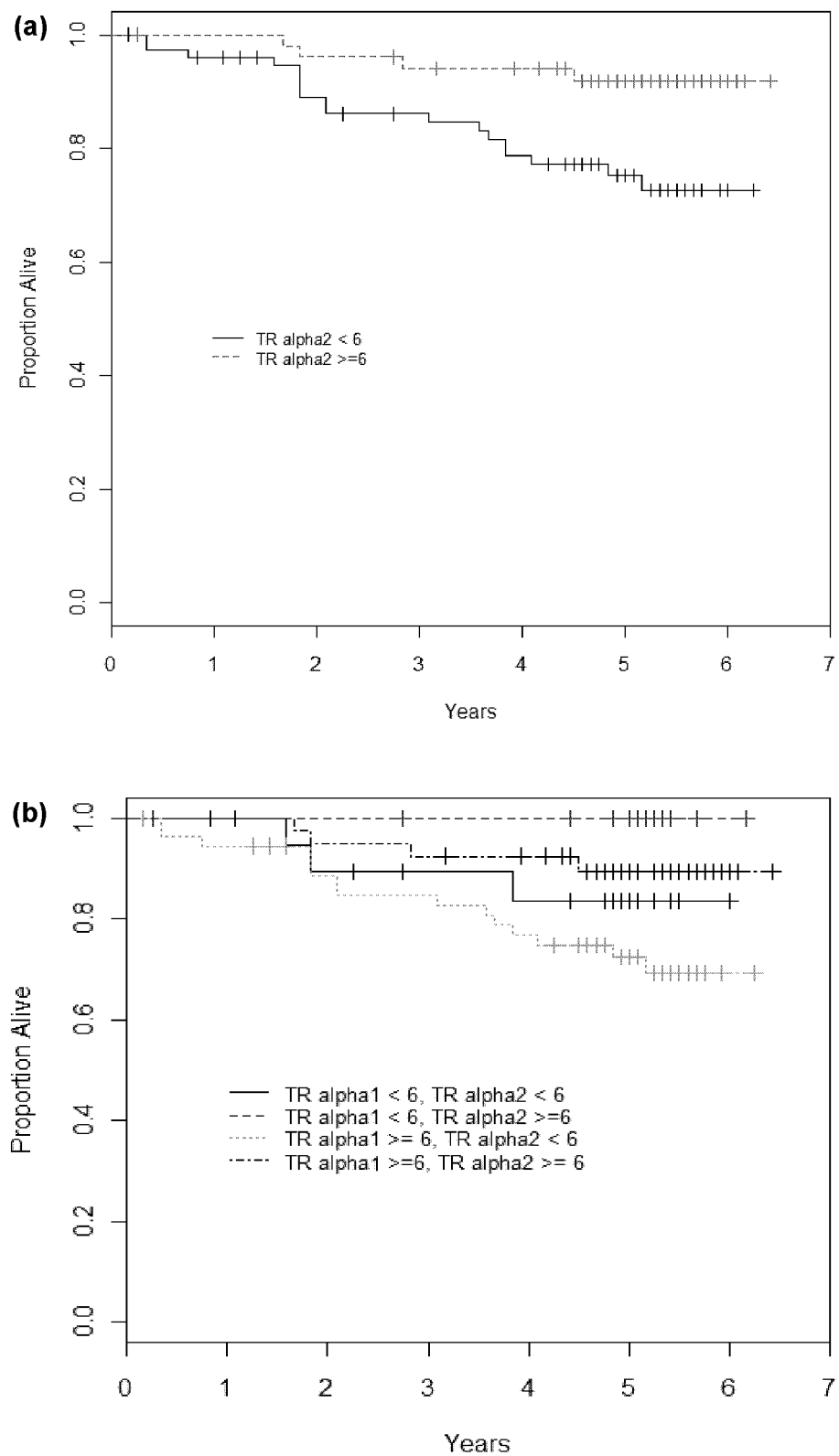
FIG. 5 (a) shows the effect of high THRα2 expression (Allred score ≥6) on overall survival of the patients (n=130), and (b) shows the effect of THRα1 and THRα2 expression on overall survival.

Using the dichotomized data (Allred score <6 or ≥6), high THRα2 expression was associated with an improved overall survival [HR 0.29 95% CI (0.10-0.85), p=0.024] (FIG. 5). Patients with low THRα2 expression had an inferior 5-year survival of 75.3% (95% CI 67.9%-87.7%) compared to those with high THRα2 expression [91.7% (95% CI 84.2%-99.9%)].

When assessed as a continuous variable, there was a significantly improved recurrence-free survival [HR 0.87 (95% CI 0.76-0.99)/unit increase in the Allred score, p=0.039] and overall survival [HR 0.84 per unit increase (95% CI 0.71-0.98), p=0.024] with increasing THRα2 expression in the univariable model. After adjusting for ER status, THRα2 remained a statistically significant prognostic variable for overall survival [HR 0.83 (95% CI 0.40-0.99), p=0.033] and for recurrence-free survival [HR 0.87 (95% CI 0.75-1.00), p=0.044] in the multivariable model.

Among patients in Cohort #2, the median expression of THRα2 based on the Allred score was 7, with a range of 0 to 8 (FIG. 4). THRα2 was highly expressed (Allred score ≥5) in the nuclei of 78% of tumors (n=117). THRα2 expression was only weakly/not (Spearman ρ<|0.30|) associated with age, tumor size and stage of disease. There was no significant association between THRα2 expression levels with grade and LVI, but THRα2 expression levels were significantly (p=0.019) different based on lymph node involvement. Amongst 32 patients with lymph node involvement, the mean (std dev) THRα2 level was 5.09 (2.52), compared with 6.28 (1.86) for the 112 patients without lymph node involvement.

There was a significantly improved RFS [HR 0.78 per unit increase (95% CI 0.68-0.90), p<0.001] and overall survival [HR 0.81 (95% CI 0.69-0.96)/unit increase in the Allred score, p=0.015] with increasing THRα2 expression in the univariable model. Results were similar when THRα2 was dichotomized with cutpoints of 4 or 5. The 5-year OS was 60.4% (95% CI 32.8%-79.6%) for women with low THRα2 (<5) expression and 82.7% (95% CI 73.9%-88.8%) for those with high (≥5) expression (Table 4b). After adjusting for stage, nodal status and treatment, THRα2 expression was not prognostic for OS (HR=0.90, 95% CI=0.71 to 1.16, p=0.42) or RFS (HR=0.86, 95% CI=0.72 to 1.04, p=0.13).

Results for Pattern of THRα Expression

Cohort #1: Overall survival according to THRα1 and THRα2 levels (dichotomised) are illustrated graphically in FIG. 5b. Among 96 patients with high THRα1 expression, the 5-year survival was 72.4% (95% CI: 61.1%-85.9%) for those 33 patients with low THRα2 expression and 89.5% (95% CI: 80.3%-99.8%) for those with high THRα2 expression. Among the patients with low THRα1 expression, the 5-year survival was 83.5% (95% CI: 68.0%-100%) amongst 21 patients who also had low THRα2 expression, while it was 100% for 12 patients with high THRα2 expression.

Cohort #2: Among 141 women with a high-degree of THRα1 expression in their tumors, the 5-year survival was 54.2% (95% CI: 25.6%-75.9%) for those 28 patients with low THRα2 expression and 83.2% (95% CI: 74.3%-89.2%) for those 111 patients with high THRα2 expression (Table 5), a difference which was statistically significant (p=0.002). Only 10 women had low THRα1 expression in their tumors, limiting further statistical analyses among this subgroup.

Discussion

Figure 6:
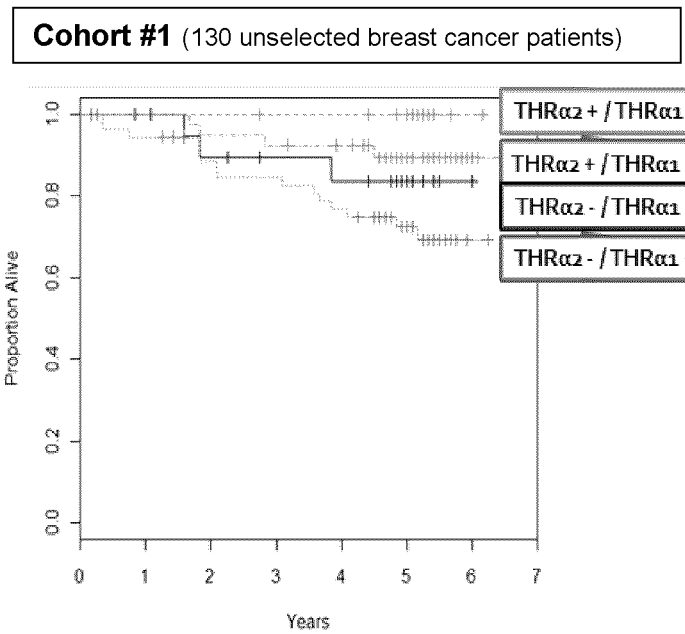
FIG. 6 shows the effect of THRα2 on overall survival in the two cohorts of women with breast cancer that were studied.
Figure 6:
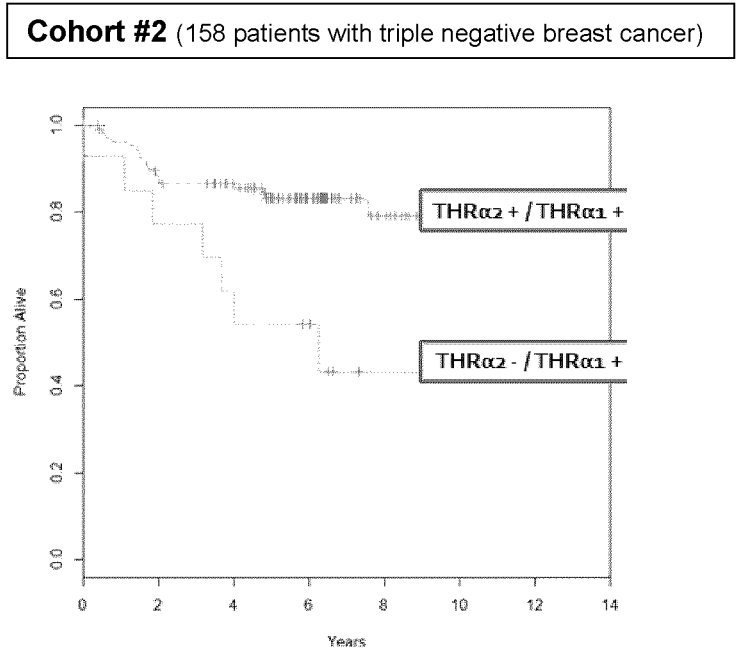

In these two retrospective cohort studies of 130 unselected (largely ER positive) breast cancer patients and 158 patients with TNBC, it was observed that thyroid hormone receptor alpha isoforms are expressed at a high level in a significant proportion of breast cancers. There was a statistically significant positive association between high THRα2 expression and overall survival, independent of known prognostic variables. In the largely ER positive cohort, those women who had low THRα1 expression and high THRα2 expression had the highest observed 5-year overall survival (100%) but the sample size was small (n=12). In the triple negative cohort #2, a very similar pattern was seen. Looking only at the women whose tumors expressed THRα1, we found that THRα2 was discriminatory in predicting overall survival (FIG. 6).

Associations between THRα2 expression [11] and (non-selective) THRα [12] expression and disease-free survival have been previously reported. Our results, based on the largest dataset to date, support a relationship between high THRα2 expression and improved outcome. Although the mechanism underlying this finding has not been determined, without wishing to be bound by theory, THRα2 may antagonize the growth-promoting effects of thyroid hormone, which are mediated by THRα1 [4-8]. Thus, THRα2 expression may result in reduced transcription of p53 and retinoblastoma, as well as other growth-promoting genes in breast cancer [13].

The finding that high THRα2 expression was inversely related to HER2 expression in cohort #1 was unexpected given that the THRA gene has been shown in one study to be co-amplified with the HER2 gene in 54.7% of HER2 positive tumors, due to the close proximity of the two genes on chromosome 17 [14]. An inverse correlation between these two markers at the protein expression level (measured by immunohistochemistry) may be explained by a number of factors including epigenetic silencing, posttranslational modification of translated proteins and the fact that not all amplified genes are over-expressed. Furthermore, it is unclear which thyroid hormone receptor isoform is primarily over-expressed due to THRA amplification [14].

Although THRα2 expression was related with ER positivity in cohort #1, the prognostic value of THRα2 was maintained after adjustment for ER, suggesting that it may be an independent prognostic marker. Cross-talk between estrogen and thyroid hormone signaling pathways [13, 15, 16] may explain the relationship between ER and THR receptors, but this has not been well studied.

The results in Tables 3a and 4a provide evidence that THRα2 is independently prognostic for both recurrence-free survival and overall survival in breast cancer patients. This supports the potential of THRα2 as a prognostic marker in breast cancer. The data also support the therapeutic potential of THRα2 induction and/or up-regulation in breast cancer. While THRα1 was not prognostic for either recurrence-free or overall survival in Tables 3a and 4a, the ratio of THRα2 and THRα1 (average THRα2/average THRα1) was independently prognostic for overall survival [HR 0.54 (95% CI 0.34-0.86), p=0.009]. Hence, the present invention also suggests a role for THRα1 as a prognostic indicator in breast cancer.

Given a very high expression of THRα1 in both cohort #1 (largely ER positive) and cohort #2 (triple negative), it is possible that breast tumors are responsive to the growth-promoting effects of thyroid hormone. Based on the findings in this study, the expression of THRα2 represses signaling that is mediated by THRα1. Therefore, among the subgroup of breast cancer patients expressing THRα1, outcomes can be improved by a) lowering the systemic levels of thyroid hormone [17-19], b) inhibiting THRα1, or c) up-regulating THRα2 [20, 21]. The possibility of lowering the systemic levels of thyroid hormone using commercially available drugs is intriguing, but further study of this potential therapy is limited by conflicting results regarding the effect of hypothyroidism in women with breast cancer [17-19, 22-29]. It is possible that the thyroid receptor expression in a breast tumor affects its response to thyroid hormone and that those expressing an "unfavorable" thyroid receptor profile may benefit from a reduction in thyroid hormone levels.

Example 2: In Vitro Evaluation of an Exemplary Compound of Formula (I) or Compound of Formula (Ia) Against Highly Expressing THRα1 Breast Cancer Cell Lines In light of the results reported in Example 1, novel approaches to breast cancer therapy may include a) lowering the systemic levels of thyroid hormone [17-19], b) inhibiting THRα1, or c) up-regulating THRα2 [20, 21]. The three approaches were evaluated through a series of in vitro experiments.

First, the role of THs on breast cancer cell proliferation was evaluated using escalating doses of tri-iodothyronine (T3) and thyroxine (T4). Next, propylthiouracil (PTU) was used to block T4 conversion to T3 demonstrating that observed proliferation was TH dependent. Finally, the anti-proliferative efficacy of a THRα1 inhibitor, a compound of Formula (I) or compound of Formula (Ia), was used to demonstrate the benefit of THRα1 downstream of TH signaling. In particular, the compound of Formula (I) or compound of Formula (Ia) is dronedarone. Dronedarone was selected as it is an FDA approved anti-arrhythmic drug.

Methods

The effect of increasing concentrations of T3 and T4 on the proliferation of 3 breast cancer cell lines (MCF 7, MD-MB-231, BT-474) in 10% charcoal-stripped phenol-free serum was evaluated at 24 and 48 hours following standard MTT-assay protocols. Increasing doses of PTU and dronedarone were added to cells with 200 µM T3 or T4 to measure proliferation of MCF-7 and MD-MB-231 cells using MTT assays.

Results & Discussion

Figure 7:
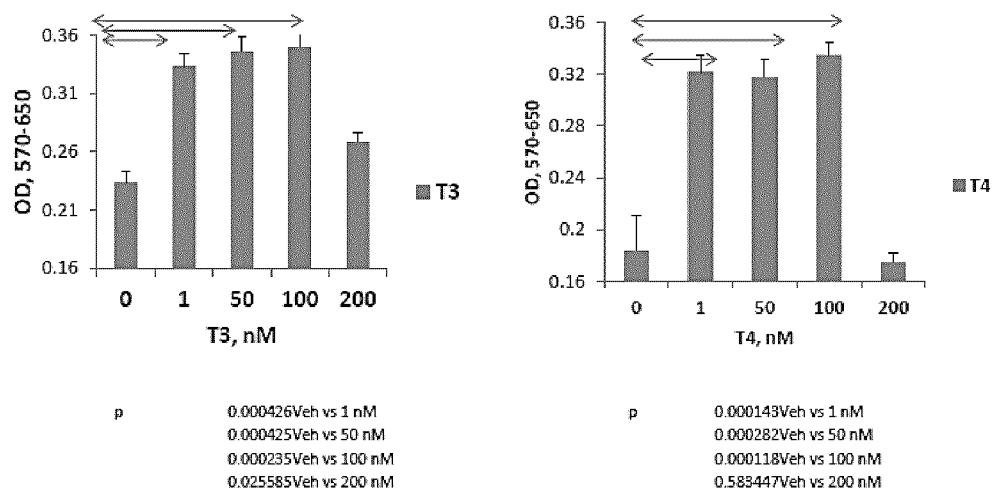
FIG. 7 shows the effect of T3 and T4 on the proliferation of MCF7 cells at 24 hours.
Figure 8:
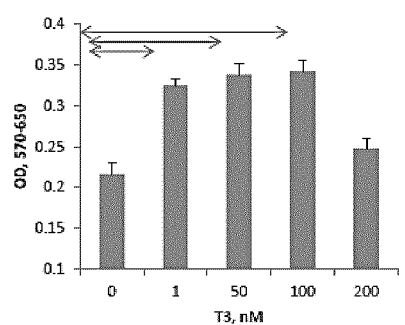
FIG. 8 shows the effect of T3 and T4 on the proliferation of MDA-MB-231 cells at 24 hours.
Figure 8:
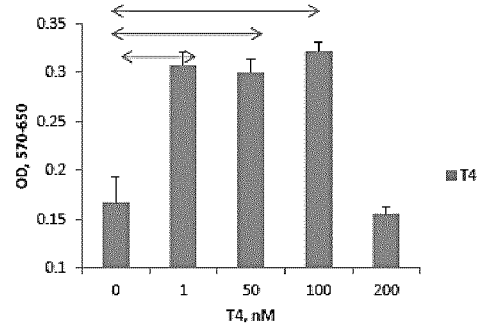
Figure 9:
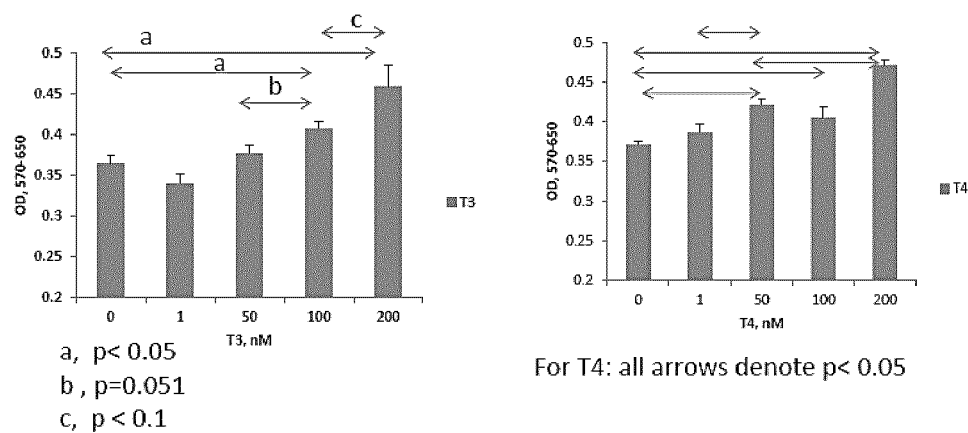
FIG. 9 shows the effect of T3 and T4 on the proliferation of BT474 cells at 48 hours.

There was a statistically significant increase in the proliferation of MCF7, MD-MB-231 and BT-474 cells with the addition of T3 and T4 at 24 and 48 hours in a dose dependent manner. Of note, BT-474 cells had a significantly slower proliferation rate and required 9 days of incubation prior to detection of proliferation. These results are illustrated in FIGS. 7, 8 and 9.

Figure 10:
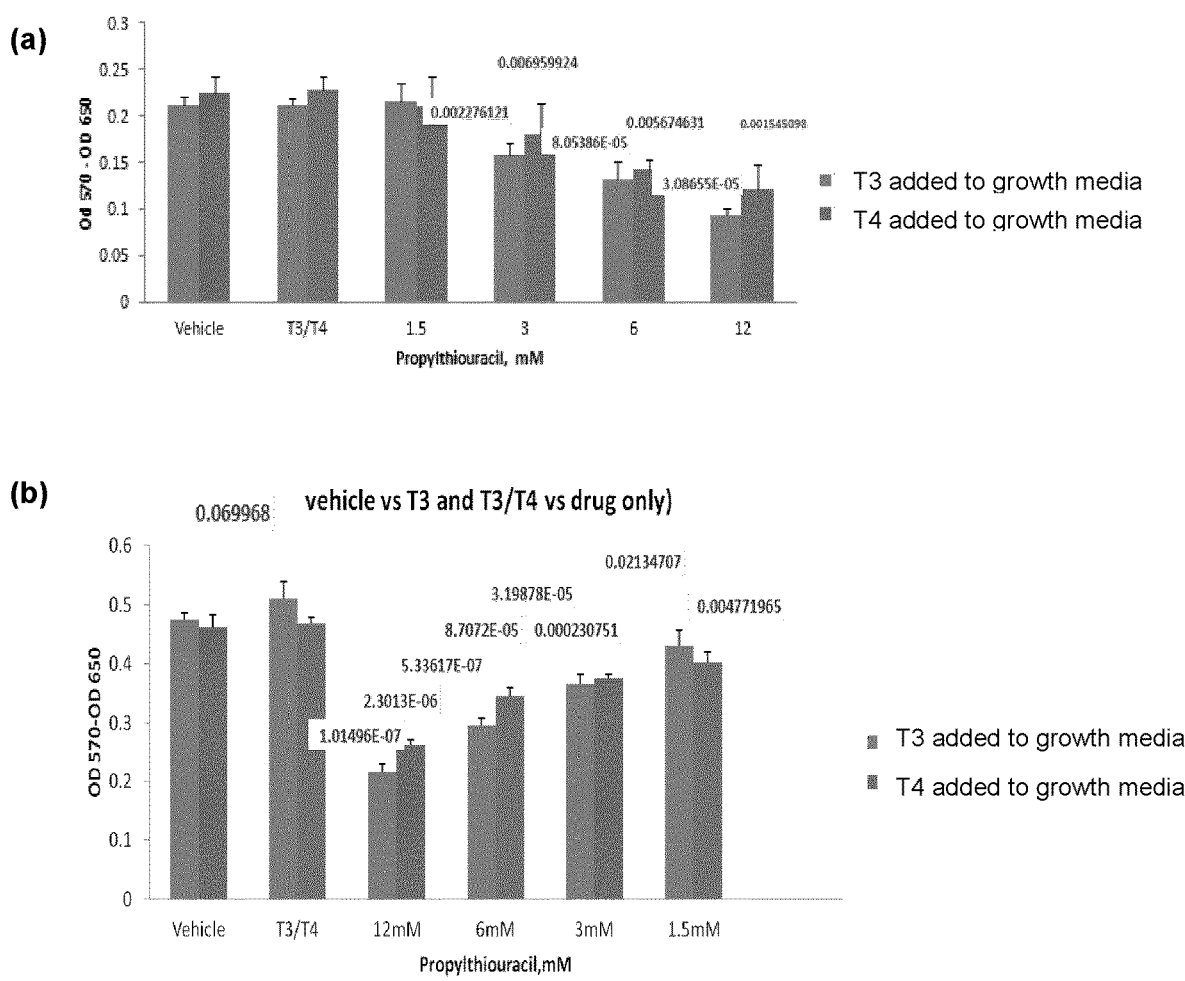
FIG. 10 (a) shows the anti-proliferative effect of propylthiouracil in combination with 100 μM of T3 and T4 in MDA-MB-231 cells at 24 hours, (b) shows the anti-proliferative effect of propylthiouracil (PTU) in combination with 100 μM of T3 and T4 in MCF7 cells at 24 hours.
Figure 11:
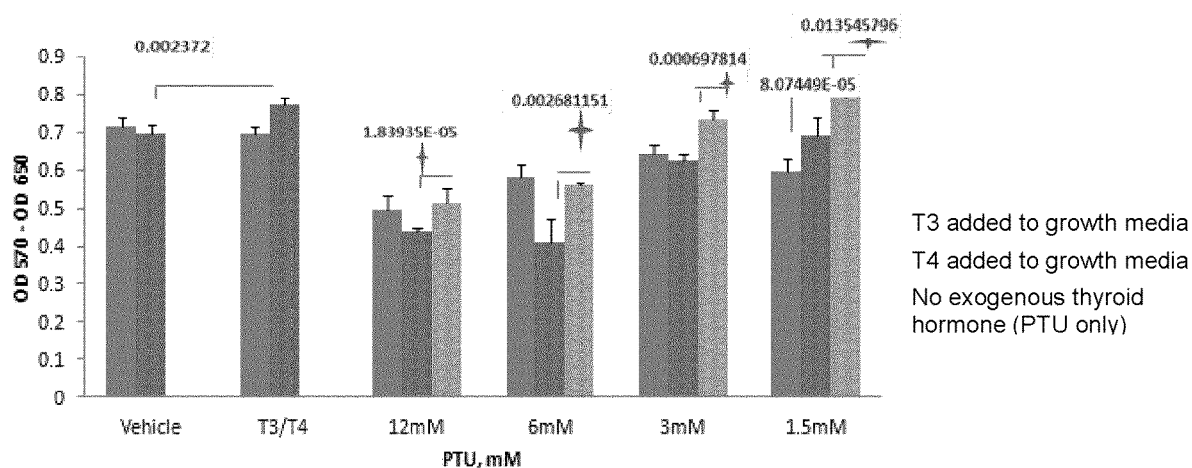
FIG. 11 shows the anti-proliferative effect of propylthiouracil (PTU) alone and in combination with 200 μM of T3 and T4 on the growth of MDA-MB-231 cells at 24 hours.

The addition of PTU reduced proliferation by 50% in MCF7 and MD-MB-231 cells in the presence of T4 at roughly 5 µM compared to the presence of T3 which had an $IC_{50}$ of 12 µM (FIG. 10). These results indicate that TH signaling is mediated by T4 conversion to T3 in these particular cell lines. PTU alone reduced cell proliferation by 50% at concentrations above 12 µM, suggesting that PTU may also act through other mechanisms (FIG. 11).

Figure 12:
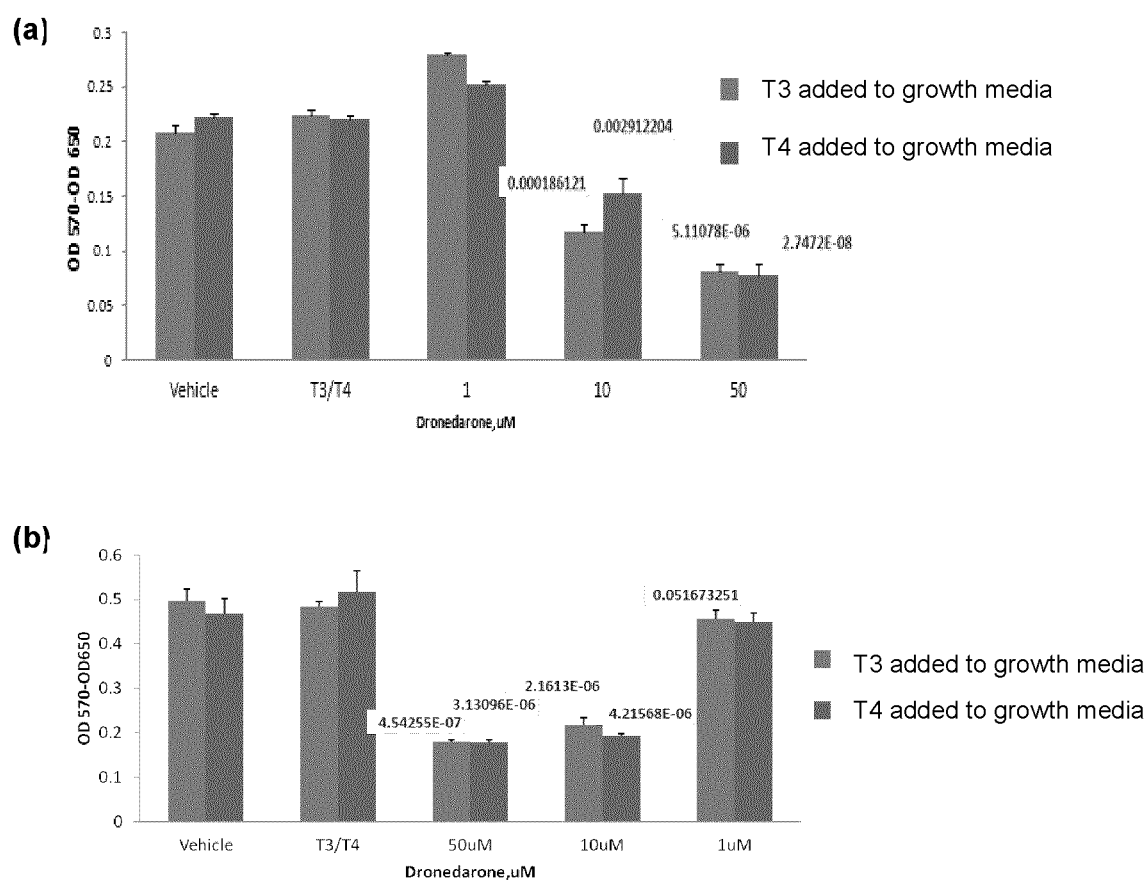
FIG. 12 (a) shows the anti-proliferative effect of Dronedarone in combination with 100 μM of T3 and T4 on MDA-MB-231 cells at 24 hours in an exemplary embodiment of the application, (b) shows the anti-proliferative effect of Dronedarone in combination with 100 μM of T3 and T4 on MCF7 cells at 24 hours in an exemplary embodiment of the application.
Figure 13:
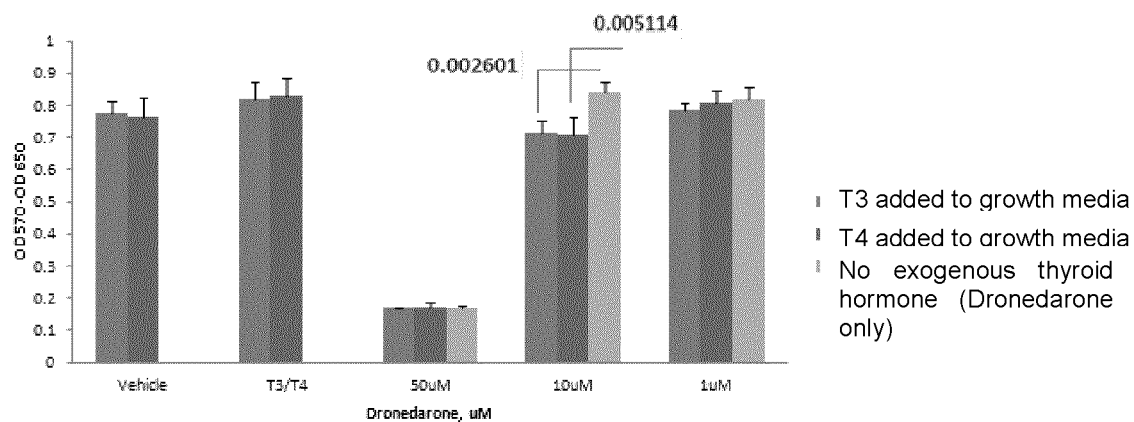
FIG. 13 shows the anti-proliferative effect of Dronedarone alone and in combination with 200 μM of T3 and T4 on the growth of MDA-MB-231 cells at 24 hours in an exemplary embodiment of the application.
Figure 14:
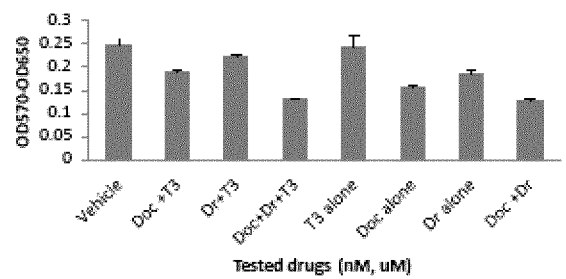
FIG. 14 shows the anti-proliferative effect of i) vehicle, ii) 200 μM Docetaxel plus 200 nM of T3, iii) 7.5 μM Dronedarone plus 200 nM of T3, iv) Combination of 200 μM Docetaxel plus 7.5 μM Dronedarone plus 200 nM of T3, v) 200 nM of T3 alone, vi) 200 μM of Docetaxel alone, vii) 7.5 μM Dronedarone alone and, viii) 200 μM of Docetaxel plus 7.5 μM of Dronedarone on the proliferation of MDA-MB-231 cells at 24 hours in exemplary embodiments of the application.
Figure 15:
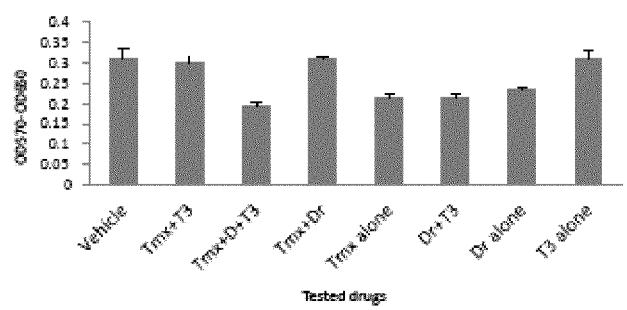
FIG. 15 shows the anti-proliferative effect of i) vehicle, ii) 7.5 μM 4-hydroxy-tamoxifen plus 200 nM of T3, iii) 7.5 μM 4-hydroxy-tamoxifen plus 7.5 μM Dronedarone plus 200 nM of T3, iv) 7.5 uM of 4-hydroxy-tamoxifen plus 7.5 μM Dronedarone, v) 7.5 μM of 4-hydroxy-tamoxifen alone, vi) 7.5 μM Dronedarone plus 200 nM of T3, vii) 7.5 μM Dronedarone alone, and viii) 200 nM of T3 alone on the proliferation of MDA-MB-231 cells at 24 hours in exemplary embodiments of the application.
Figure 16:
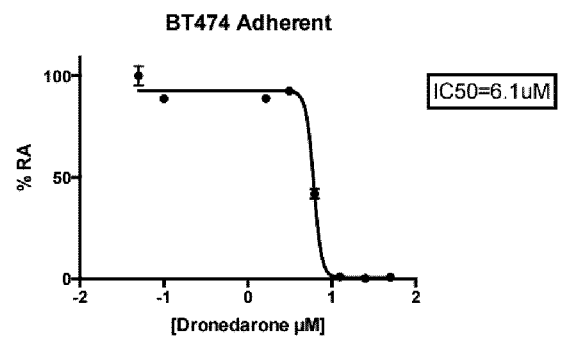
FIG. 16 (a)-(d) shows the $IC_{50}$ of dronedarone in a series of sphere-forming assays using (a). BT474 cells, (b) MDA MB 157 cells, (c) BT20 cells and (d) MDA MB 453 cells in exemplary embodiments of the application.
Figure 16:
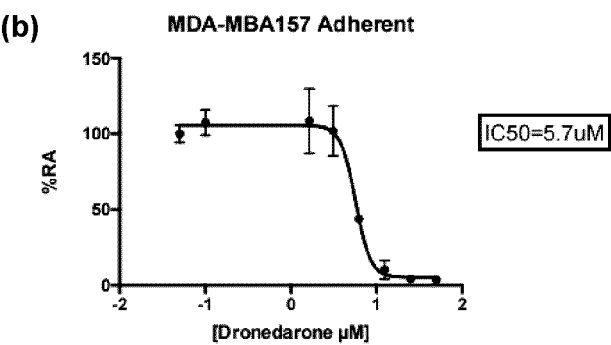
Figure 16:
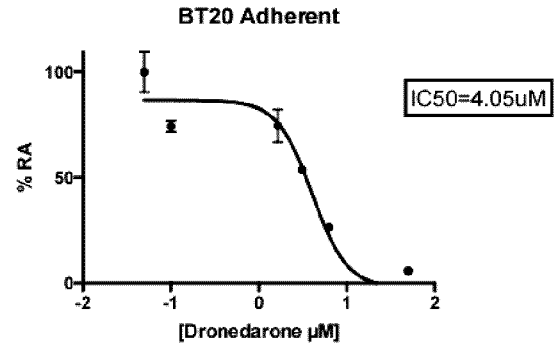
Figure 16:
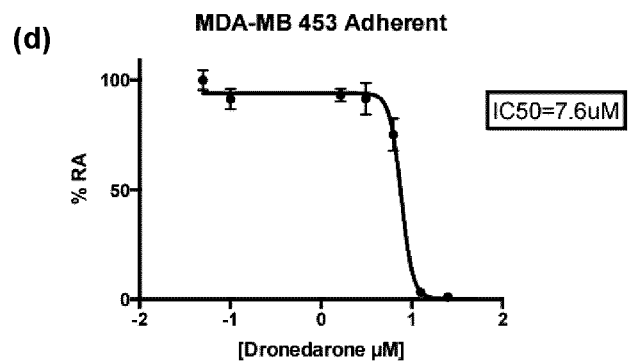

Cell proliferation was not affected by the presence of dronedarone alone, but the combination of 10 µM dronedarone and T3 or T4 which significantly reduced proliferation of both MCF7 and MD-MB-231 cells (FIGS. 12 and 13, respectively). These results suggest that THRα1 is involved in TH mediated cell proliferation.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| a) Characteristics of assessed breast tumors (Cohort #1) | | | |
|---|---|---|---|
| Characteristic | Statistic | N | Result, n (%) |
| Age at Diagnosis | Mean (std) | 130 | 65.1 (14.8) |
| Tumour Characteristics | | | |
| Tumour Size | Median (range) | 129 | 2.8 (1-10.2) |
| Nodal stage | 0 | 113 | 62 (54.9) |
| | 1 | | 41 (36.3) |
| | 2 | | 7 (6.2) |
| | 3 | | 3 (2.7) |
| T stage | 1 | 130 | 40 (30.8) |
| | 2 | | 73 (56.2) |
| | 3 | | 16 (12.3) |
| | 4 | | 1 (0.8) |
| Stage | 1 | 113 | 24 (21.2) |
| | 2 | | 69 (61.1) |
| | 3 | | 20 (17.7) |
| Grade | I | 130 | 27 (20.8) |
| | II | | 70 (53.9) |
| | III | | 32 (24.6) |
| | Missing | | 1 (0.8) |
| ER Status | N (%) Positive | 130 | 95 (73.1) |
| PR Status | N (%) Positive | 130 | 77 (59.2) |
| HER2 Status | N (%) Positive | 129 | 17 (13.2) |
| Triple Negative | N (%) Triple Negative | 130 | 28 (21.5) |
| Avg THRα1 | Median (range) | 129 | 7 (0-8) |
| | N (%) ≥6 | | 96 (74.4) |
| Avg THRα2 | Median (range) | 129 | 5 (0-8) |
| | N (%) ≥6 | | 52 (40.3) |
| Lymphovascular Invasion | N (%) | 129 | 30 (23.3) |
| Mitotic Count | Median (range) | 130 | 7.5 (0-51) |

TABLE 1-continued a) Characteristics of assessed breast tumors (Cohort #1)

| Characteristic | Statistic | N | Result, n (%) |
|---|---|---|---|
| Treatment | | | |
| Hypothyroid | N (%) | 130 | 16 (12.3) |
| Chemotherapy Alone | N (%) | 124 | 24 (19.4) |
| Hormone Therapy Alone | | | 43 (34.7) |
| Chemo & Hormone Therapy | | | 35 (28.2) |
| Neither | | | 22 (17.7) |
| Outcomes | | | |
| Overall Survival | N (%) Deaths | 130 | 22 (16.9) |
| | 2-year OS | | 91.9 (85.5-95.6) |
| | 5-year OS | | 82.3 (74.0-88.1) |
| Recurrence-Free Survival | N (%) Events | 130 | 36 (27.7) |
| | 2-year RFS | | 84.9 (77.4-90.1) |
| | 5-year RFS | | 74.0 (65.3-80.9) |

TABLE 1 b) Characteristics of assessed breast tumors (Cohort #1)

| Characteristic | Statistic | N | Result |
|---|---|---|---|
| Baseline Characteristics | | | |
| Age | Mean (std) | 159 | 61.4 (14.9) |
| Tumour Characteristics | | | |
| Tumour Size | Median (range) | 159 | 2.7 (0-10) |
| Node Positive | N (%) | 145 | 33 (22.8) |
| Stage | N (%) 3 or 4 | 154 | 19 (12.3) |
| Grade | I | 159 | 4 (2.5) |
| | II | | 33 (20.8) |
| | III | | 122 (76.7) |
| THRα1 | Median (range) | 152 | 7 (3-8) |
| | N (%) ≥4 | | 148 (97.4) |
| | N (%) ≥5 | | 142 (93.4) |
| | N (%) ≥7 | | 100 (65.8) |
| THRα2 | Median (range) | 150 | 7 (0-8) |
| | N (%) ≥4 | | 131 (87.3) |
| | N (%) ≥5 | | 117 (78.0) |
| | N (%) ≥7 | | 84 (56.0) |
| Lymphovascular Invasion | N (%) | 157 | 38 (24.2) |
| Prior Treatment | | | |
| Chemotherapy | N (%) | 155 | 116 (74.8) |
| Radiation | N (%) | 153 | 103 (67.3) |
| Chemotherapy Alone | N (%)* | 153 | 31 (20.3) |
| Radiation Alone | | | 18 (11.8) |
| Chemoradiation | | | 85 (55.6) |
| Neither | | | 19 (12.4) |
| Outcomes | | | |
| Overall Survival | N (%) Deaths | 157 | 28 (17.8) |
| | 2-year OS | | 85.8 (78.6-90.7) |
| | 5-year OS | | 80.6 (72.6-86.5) |
| Recurrence-Free Survival | N (%) Events | 158 | 39 (24.7) |
| | 2-year RFS | | 82.0 (74.5-87.5) |
| | 5-year RFS | | 73.7 (65.2-80.4) |

TABLE 2

Pathological and clinical associations with thyroid hormone receptor expression for Cohort #1.

| Characteristic | Statistic | N | Mean (SD) THRα1 | ρ | Mean (SD) THRα2 | ρ |
|---|---|---|---|---|---|---|
| Nodal stage | 0 | 61 | 6.3 (1.8) | −0.12 | 4.8 (2.4) | −0.07 |
| | 1 | 41 | 6.1 (1.8) | | 4.5 (2.5) | |
| | 2 | 7 | 5.8 (2.1) | | 5.1 (2.3) | |
| | 3 | 3 | 4.5 (3.0) | | 3.6 (0.7) | |
| T stage | 1 | 40 | 6.3 (2.0) | 0.02 | 5.1 (2.4) | −0.11 |
| | 2 | 72 | 6.2 (1.7) | | 4.7 (2.5) | |
| | 3 | 16 | 6.6 (1.7) | | 4.5 (2.4) | |
| Stage | 1 | 24 | 6.3 (2.0) | 0.03 | 5.2 (2.3) | −0.10 |
| | 2 | 68 | 6.1 (1.7) | | 4.6 (2.5) | |
| | 3 | 20 | 6.4 (2.0) | | 4.6 (2.1) | |
| Grade | I | 27 | 6.3 (1.8) | −0.13 | 5.2 (2.5) | −0.31 |
| | II | 69 | 6.4 (1.8) | | 5.2 (2.3) | |
| | III | 32 | 5.8 (1.7) | | 3.3 (2.2) | |
| Age | | | | 0.16 | | 0.04 |
| Tumor Size | | | | 0.04 | | −0.06 |

| Characteristic | Statistic | N | Mean (SD) THRα1 | p-value | Mean (SD) THRα2 | p-value |
|---|---|---|---|---|---|---|
| ER Status | Negative | 34 | 6.3 (1.6) | 0.95 | 3.1 (2.0) | <0.001 |
| | Positive | 95 | 6.3 (1.9) | | 5.4 (2.3) | |

TABLE 2-continued

Pathological and clinical associations with thyroid hormone receptor expression for Cohort #1.

| | | | | | | |
|---|---|---|---|---|---|---|
| PR Status | Negative | 52 | 6.2 (1.9) | 0.89 | 3.4 (2.2) | <0.001 |
| | Positive | 77 | 6.3 (1.8) | | 5.7 (2.2) | |
| HER2 Status | Negative | 111 | 6.3 (1.8) | 0.76 | 5.0 (2.4) | 0.018 |
| | Positive | 17 | 6.1 (1.9) | | 3.5 (2.2) | |
| Lymphovascular Invasion | No | 98 | 6.3 (1.8) | 0.59 | 4.6 (2.6) | 0.27 |
| | Yes | 30 | 6.1 (1.9) | | 5.1 (2.0) | |
| Hypothyroid | No | 113 | 6.2 (1.9) | 0.20 | 4.7 (2.5) | 0.46 |
| | Yes | 16 | 6.7 (1.4) | | 5.1 (1.8) | |
| Chemotherapy | No | 65 | 6.4 (2.1) | 0.55 | 5.2 (2.6) | 0.10 |
| | Yes | 58 | 6.2 (1.5) | | 4.5 (2.2) | |
| Hormone Therapy | No | 45 | 6.3 (1.8) | 0.89 | 4.2 (2.4) | 0.026 |
| | Yes | 78 | 6.3 (1.8) | | 5.2 (2.4) | |

TABLE 3 a) Hazard Ratios for the Recurrence-Free Survival Outcome Associated with Various Clinical Parameters in Cohort #1.

| Characteristic | Description | Hazard Ratio (95% CI) | p-value |
|---|---|---|---|
| *Univariate Analysis* | | | |
| Age at Diagnosis | /10-Years | 1.48 (1.14-1.91) | 0.003 |
| Tumour Size | Log-transformed | 1.36 (0.72-2.60) | 0.35 |
| Nodal stage | /Stage | 2.31 (1.50-3.54) | <0.001 |
| T stage | /Stage | 1.10 (0.66-1.85) | 0.71 |
| Stage | /Stage | 2.02 (1.09-3.76) | 0.027 |
| Grade | /Grade | 0.92 (0.56-1.50) | 0.72 |
| ER Status | Yes | 1.33 (0.60-2.96) | 0.49 |
| PR Status | Yes | 0.87 (0.44-1.72) | 0.70 |
| HER2 Status | Yes | 1.55 (0.66-3.63) | 0.31 |
| Avg THRα1 | /unit | 1.00 (0.82-1.22) | 0.99 |
| Avg THRα1 | ≥6 | 1.01 (0.45-2.23) | 0.99 |
| Avg THRα2 | /unit | 0.90 (0.79-1.03) | 0.12 |
| Avg THRα2 | ≥6 | 0.55 (0.26-1.14) | 0.11 |
| Avg THRα2/Avg THRα1 ratio | Log-transformed | 0.75 (0.51-1.09) | 0.12 |
| Lymphovascular Invasion | Yes | 1.87 (0.90-3.89) | 0.092 |
| Mitotic Count | Log-transformed | 0.96 (0.71-1.29) | 0.78 |
| Hypothyroid | Yes | 2.22 (0.99-5.00) | 0.054 |
| Chemotherapy | Yes | 0.45 (0.22-0.94) | 0.033 |
| Hormone Theapy | Yes | 1.50 (0.71-3.16) | 0.29 |
| *Multivariate Analysis\* (n = 128)* | | | |
| Age at Diagnosis | /10-Years | 1.81 (1.33-2.46) | <0.001 |
| Lymphovascular Invasion | Yes | 3.52 (1.59-7.77) | 0.002 |
| Avg THRα2 | /unit | 0.87 (0.76-0.99) | 0.039 |
| *Multivariate Analysis\* (n = 113)* | | | |
| Nodal stage | /Stage | 2.39 (1.55-3.69) | <0.001 |
| Age at Diagnosis | /10-Years | 1.62 (1.15-2.28) | 0.006 |

*Multivariate model was constructed using forward stepwise selection from all eligible variables, except: treatment parameters (chemotherapy and hormone therapy) were not eligible as they occurred post-baseline and they are based on a clinical decision; nodal status and overall stage were excluded due to the number of missing data points and the high presumed correlation with overall grade.
‡ Given the significance of N stage univariately, a second MVA was run including N grade as a potential covariate

TABLE 3 b) Hazard Ratios for the Recurrence-Free Survival Outcome Associated with Various Clinical Parameters in triple negative breast cancer (Cohort #2).

| Characteristic | Description | N | Hazard Ratio (95% CI) | p-value |
|---|---|---|---|---|
| *Univariate Analysis* | | | | |
| Age | /10-Years | 158 | 1.53 (1.19-1.97) | <0.001 |
| Tumour Size | Log-transformed | 156 | 1.97 (1.08-3.60) | 0.027 |
| Node Positive | Yes | 145 | 8.28 (4.01-17.10) | <0.001 |
| Stage | 3 or 4 | 153 | 10.68 (5.49-20.79) | <0.001 |
| Grade | 3 | 158 | 0.51 (0.27-0.97) | 0.041 |
| Lymphovascular Invasion | Yes | 156 | 2.52 (1.33-4.77) | 0.005 |
| Treatment | Chemotherapy | 154 | 0.39 (0.20-0.75) | 0.005 |
| | Radiation | 152 | 0.35 (0.19-0.67) | 0.002 |
| THRα1 | Continuous | 151 | 0.86 (0.63-1.16) | 0.31 |
| THRα2 | Continuous | 149 | 0.78 (0.68-0.90) | <0.001 |
| | ≥4 | | 0.32 (0.14-0.74) | 0.008 |
| | ≥5 | | 0.24 (0.12-0.47) | <0.001 |
| | ≥7 | | 0.68 (0.36-1.31) | 0.25 |
| *Multivariate Analysis* | | | | |
| Stage | 3 or 4 | 142 | 5.78 (1.92-17.42) | 0.002 |
| Node Positive | Yes | | 3.12 (1.01-9.61) | 0.047 |
| Treatment | Chemotherapy | | 0.32 (0.14-0.73) | 0.007 |

* After adjusting for stage, node and treatment, neither THRα1 (p = 0.16) nor THRα2 was significant (p = 0.13)

TABLE 4 a) Hazard Ratios for Overall Survival Outcome Associated with Various Clinical Parameters in Cohort #1.

| Characteristic | Description | Hazard Ratio (95% CI) | p-value |
|---|---|---|---|
| *Univariate Analysis* | | | |
| Age at Diagnosis | /10-Years | 1.56 (1.12-2.17) | 0.009 |
| Tumour Size | Log-transformed | 1.78 (0.80-3.98) | 0.16 |
| Nodal stage | /Stage | 1.87 (1.09-3.20) | 0.024 |
| T stage | /Stage | 1.55 (0.82-2.95) | 0.18 |
| Stage | /Stage | 1.74 (0.85-3.60) | 0.13 |
| Grade | /Grade | 1.17 (0.62-2.21) | 0.63 |
| ER Status | Yes | 0.77 (0.32-1.90) | 0.57 |
| PR Status | Yes | 0.43 (0.19-1.01) | 0.054 |
| Her2 Status | Yes | 1.57 (0.53-4.68) | 0.41 |
| Avg TR α1 | /unit | 1.16 (0.87-1.55) | 0.31 |
| Avg TR α1 | ≥6 | 2.08 (0.62-7.04) | 0.24 |
| Avg TR α2 | /unit | 0.84 (0.71-0.98) | 0.029 |
| Avg TR α2 | ≥6 | 0.29 (0.10-0.85) | 0.024 |
| Avg TR α2/Avg TR α1 ratio | Log-transformed | 0.62 (0.40-0.94) | 0.025 |

TABLE 4-continued a) Hazard Ratios for Overall Survival Outcome Associated with Various Clinical Parameters in Cohort #1.

| Characteristic | Description | Hazard Ratio (95% CI) | p-value |
|---|---|---|---|
| Avg TR β1 nuclear | Yes | 1.64 (0.22-12.27) | 0.63 |
| Avg TR β1 cytoplasmic | /unit | 0.85 (0.66-1.09) | 0.19 |
| Lymphovascular Invasion | Yes | 0.79 (0.27-2.36) | 0.68 |
| Mitotic Count | Log-transformed | 0.97 (0.67-1.41) | 0.86 |
| Hypothyroid | Yes | 3.40 (1.33-8.72) | 0.011 |
| Chemotherapy | Yes | 0.71 (0.30-1.69) | 0.44 |
| Hormone Therapy | Yes | 0.95 (0.39-2.29) | 0.90 |
| Multivariate Analysis* (n = 129) | | | |
| Hypothyroid | Yes | 4.24 (1.58-11.41) | 0.004 |
| Avg TR α2/Avg TR α1 ratio | Log-transformed | 0.54 (0.34-0.86) | 0.009 |
| Multivariate Analysis* (n = 110) | | | |
| Hypothyroid | Yes | 3.75 (1.26-11.12) | 0.017 |
| Avg TR α2 | /unit | 0.78 (0.64-0.95) | 0.015 |
| Nodal stage | /Stage | 2.90 (1.48-5.67) | 0.002 |
| Age at Diagnosis | /10-Years | 1.58 (1.00-2.48) | 0.048 |

*Multivariate model was constructed using forward stepwise selection from all eligible variables, except: treatment parameters (chemotherapy and hormone therapy) were not eligible as they occurred post-baseline and they are based on a clinical decision; overall stage was excluded due to the number of missing data points and the high presumed correlation with overall grade. Nodal status was included as a potential covariate.
‡ Given the significance of N stage univariately, a second MVA was run including N grade as a potential covariate

TABLE 4 b) Hazard Ratios for the Overall Survival Outcome Associated with Various Clinical Parameters in Triple negative breast cancer (Cohort #2).

| Characteristic | Description | N | Hazard Ratio (95% CI) | p-value |
|---|---|---|---|---|
| Univariate Analysis | | | | |
| Age | /10-Years | 157 | 1.72 (1.26-2.34) | <0.001 |
| Tumour Size | Log transformed | 155 | 2.76 (1.33-5.73) | 0.007 |
| Node Positive | Yes | 144 | 23.23 (7.85-68.75) | <0.001 |
| Stage | 3 or 4 | 152 | 13.67 (6.18-30.26) | <0.001 |
| Grade | 3 | 157 | 0.71 (0.32-1.57) | 0.40 |
| Lymphovascular Invasion | Yes | 155 | 3.54 (1.68-7.45) | <0.001 |
| Treatment | Chemotherapy | 153 | 0.26 (0.12-0.55) | <0.001 |
|  | Radiation | 151 | 0.44 (0.21-0.92) | 0.030 |
| THRα1 | Continuous | 151 | 0.86 (0.62-1.18) | 0.34 |
| THRα2 | Continuous | 149 | 0.81 (0.69-0.96) | 0.015 |
|  | ≥4 |  | 0.51 (0.18-1.47) | 0.21 |
|  | ≥5 |  | 0.36 (0.16-0.83) | 0.017 |
|  | ≥7 |  | 0.81 (0.38-1.72) | 0.58 |
| Multivariate Analysis | | | | |
| Stage | 3 or 4 | 141 | 6.02 (1.98-18.24) | 0.002 |
| Node Positive | Yes |  | 10.58 (2.85-39.20) | <0.001 |
| Treatment | Chemotherapy |  | 0.16 (0.06-0.42) | <0.001 |

* After adjusting for stage, node and treatment, neither THRα1 (p = 0.40) nor THRα2 was significant (p = 0.42)

TABLE 5

Overall Survival Outcomes Based on THRα1 and THRα2 categories in triple negative breast cancer patients (cohort #2).

| Characteristic | Statistic | | N | Result |
|---|---|---|---|---|
| THRα2 | ≤4 | N (%) Deaths | 33 | 8 (24.2%) |
|  |  | 2-year OS |  | 80.5% (53.3-92.8) |
|  |  | 5-year OS |  | 60.4% (32.8-79.6) |
|  | ≥5 | N (%) Deaths | 116 | 20 (17.2%) |
|  |  | 2-year OS |  | 86.1% (78.0-91.4) |
|  |  | 5-year OS |  | 82.7% (73.9-88.8) |
| THRα1 | ≤4 | N (%) Deaths | 10 | 1 (10.0%) |
|  |  | 2-year OS |  | 80.0% (20.4-96.9) |
|  |  | 5-year OS |  | 80.0% (20.4-96.9) |
|  | ≥5 | N (%) Deaths | 141 | 27 (19.2%) |
|  |  | 2-year OS |  | 85.3% (77.7-90.5) |
|  |  | 5-year OS |  | 79.7% (71.1-85.9) |

REFERENCES

1. Jerzak K J, Cockburn J, Pond G R, Pritchard K I, Narod S A, et al. (2015) Thyroid hormone receptor α in breast cancer: prognostic and therapeutic implications. Breast Cancer Res Treat. 149(1):293-301.
2. Alvarado-Pisani A R, Chacon R S, Betancourt L J et al. (1986) Thyroid hormone receptors in human breast cancer: effect of thyroxine administration. Anticancer Res 6: 1347-1351.
3. Iberiro R C J, Apriletti J W, Wagner R L, Feng W, Kushner P J, et al. (1998) X-ray Crystallographic and Functional Studies of Thyroid Hormone Receptor. J Steroid Biochem Molec Biol. 65 (1): 133-141.
4. THRA thyroid hormone receptor, alpha. National Centre for Biotechnology Information. http://www.ncbi.nlm.nih.gov/gene/7067. Accessed 15 Jul. 2014.
5. Lazar J, Desvergne B, Zimmerman E, Zimmer D B, Magnuson M A, et al. (1994) A Role for Intronic Sequences on Expression of Thyroid Hormone Receptor α Gene. The Journal of Biological Chemistry 269(32): 20352-20359.
6. Mitsuhashi T, Tennyson G E, Nikodem V M. (1988) Alternative splicing generates messages encoding rat c-erbA proteins that do not bind thyroid hormone. Proc Natl Acad Sci USA 85(16):5804-8.
7. Lazar M A, Hoin R A, Darling D S, Chin W W. (1988) Identification of a rat c-erbA alpha-related protein which binds deoxyribonucleic acid but does not bind thyroid hormone. Mol Endocrinol 2:893-901.
8. Izumo S and Mandavi V. (1988) Thyroid hormone receptor alpha isoforms generated by alternative splicing differentially active myosin HC gene transcription. Nature 334(6182):539-42.
9. Dinda S, Sanchez A, Moudgil V. (2002) Estrogen-like effects of thyroid hormone on the regulation of tumor suppressor proteins, p53 and retinoblastoma, in breast cancer cells. Oncogene. 21, 5: 5761-8.
10. Allred D C, Harvey J M, Berardo M, Clark G M. (1998) Prognostic and predictive factors in breast cancer by immunohistochemical analysis. Mol Pathol. 11(2): 155-68.
11. Smallridge R C and Latham K R (1980) Nuclear thyroid hormone receptor in human breast tumours. Clinical Res 28: 421.
12. Ditch N, Toth B, Himsl I, Lenhard M, Ochsenkuhn, Friese K, Mayr D, Jeschke U (2013) Thyroid hormone receptor (TR)alpha and TRbeta expression in breast cancer. Histol Histopathol 28:227-237.

13. Dinda S, Sanchez A, Moudgil V. (2002) Estrogen-like effects of thyroid hormone on the regulation of tumor suppressor proteins, p53 and retinoblastoma, in breast cancer cells. Oncogene, 21(5), 5761-8.
14. Lamy P-J, Fina F, Bascoul-Mollevi C, Laberenne A-C, Martin P-M, et al. (2011) Quantification and clinical relevance of gene amplification at chromosome 17q12-q21in human epidermal growth factor receptor 2-amplified breast cancers. Breast Cancer Research 13:R15.
15. Nogueira C R and Brentani M M. Triiodothyronine Mimics the Effects of Estrogen in Breast Cancer Cell Lines. J. Steroid Biochem. Molec. Biol 1996; 59: 271-279.
16. Vasudevan N, Koibuchi N, Chin W W, Pfaff D W. (2001) Differential crosstalk between estrogen receptor (ER) alpha and ERbeta and the thyroid hormone receptor isoforms results in flexible regulation of the consensus ERE. Brain Res Mol Brain Res 95:9-17.
17. Hercbergs A A, Goyal L K, Suh J H, Lee S, Reddy C A, et al. (2003) Propylthiouracil-induced chemical hypothyroidism with high-dose tamoxifen prolongs survival in recurrent high grade glioma: a phase I/II study. Anticancer Res 23: 617-626.
18. Hercbergs A (1999) Spontaneous remission of cancer—a thyroid hormone dependent phenomenon? Anticancer Res 19: 4839-44.
19. Hercbergs A, Johnson R E, Ashur-Fabian O, Garfield D H, Davis P J. (2014) Medically Induced Euthyroid Hypothyroxinemia May Extend Survival in Compassionate Need Cancer Patients: An Observational Study. Oncologist 2014-0308.
20. Gu G, Covington K R, Rechoum Y, Fuqua S A W (2012) Restoration of receptor α in triple negative breast cancer via targeting of thyroid hormone. Cancer Res 72(24 Suppl)49s.
21. Sabnis G J, Goloubeva O, Chumsri S, Nguyen N, Sukumar S, Brodie A M H (2011) Functional Activation of the Estrogen-α and Aromatase by the HDAC Inhibitor Entinostat Sensitizes ER-Negative Tumours to Letrozole. Cancer Res 71(5): 1893-903.
22. Angelousi A G, Anagnostou V K, Stamatakos M K, Georgiopoulos G A, Kontzoglou K C (2012) Primary H T and risk for breast cancer: a systematic review and meta-analysis. Eur. J. Endocrinol. 166: 373-381.
23. Davis P J, Lin Y-Y, Mousa S A, Luidens M K, Hercbergs A A, Wehling M, Davis F B (2011) Overlapping nongenomic and genomic actions of thyroid hormone and steroids. Steroids 76:829-833.
24. Tang H Y, Lin H Y, Zhang S, Davis F B, Davis P J (2004) Thyroid hormone causes mitogen-activated protein kinase-dependent phosphorylation of the nuclear estrogen receptor. Endocrinology 145:3265-3272.
25. Furuya F, Shimura H, Yamashita S, Endo T, Kobayashi T (2010) Liganded Thyroid Hormone Receptor-α Enhances Proliferation of Pancreatic β-Cells J Biol Chem 285:24477-24486.
26. Hellevik A I, Asvold B O, Bjoro T, Romundstad P R, Nilsen T I L, Vatten L J (2009) Thyroid Function and Cancer Risk: A Prospective Population Study. Cancer Epidemiol Biomarkers Prev 18:570-574.
27. Tosovic A, Bondeson A G, Bondeson L, Ericsson U B, Malm J, et al. (2010) Prospectively measured triiodothyronine levels are positively associated with breast cancer risk in postmenopausal women. Breast Cancer Res 12(3): R33.
28. De Sibio M T, de Oliveira M, Moretto F C, Olimpio R M, Conde et al. (2014) Triiodothyronine and breast cancer. World J Clin Oncol 5(3):503-8.
29. Sandhu M K, Brezden-Masley C, Lipscombe L L, Zagorski B, Booth G L. (2009) Autoimmune hypothyroidism and breast cancer in the elderly. Breast Cancer Res Treat 115(3):635-41.

The invention claimed is:

1. A method of treating breast cancer, comprising administering an effective amount of a compound (dronedarone) having the following structure:

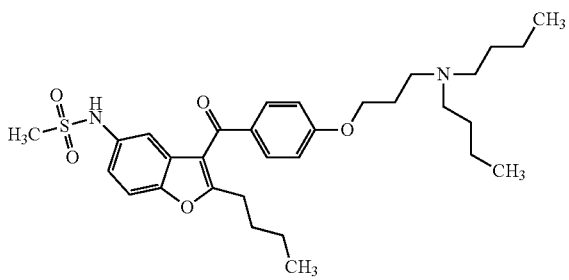 [SMILES: CCCCc1oc2ccc(NS(C)(=O)=O)cc2c1C(=O)c1ccc(OCCCN(CCCC)CCCC)cc1]

or a pharmaceutically acceptable salt and/or solvate thereof, to a subject in need thereof.

2. The method of claim 1 further comprising administering to the subject in need thereof, one or more other therapies for treating breast cancer.

3. The method of claim 2, wherein the one or more other therapies is a chemotherapy which comprises administering to the subject one or more chemical agents selected from an alkylating agent, antimetabolite, anthracycline, antitumor antibiotic, monoclonal antibody, platinum-based derivative, anti-HER2 compounds and plant alkaloid.

* * * * *